US010473558B2

(12) United States Patent
Adiga et al.

(10) Patent No.: US 10,473,558 B2
(45) Date of Patent: Nov. 12, 2019

(54) AUTOMATED HIGH SPEED METALLOGRAPHIC SYSTEM

(71) Applicants: Umesha P. S. Adiga, Centerville, OH (US); Daylond J. Hooper, Fairborn, OH (US); Nina Joshi, Xenia, OH (US); Daniel S. Banks, Franklin, OH (US); Murali K. Gorantla, Beavercreek, OH (US); Roland Adrian Hogendoorn, Dayton, OH (US); Elizabeth J. Jenkins, Springboro, OH (US); Robert F. Ondera, Casstown, OH (US)

(72) Inventors: Umesha P. S. Adiga, Centerville, OH (US); Daylond J. Hooper, Fairborn, OH (US); Nina Joshi, Xenia, OH (US); Daniel S. Banks, Franklin, OH (US); Murali K. Gorantla, Beavercreek, OH (US); Roland Adrian Hogendoorn, Dayton, OH (US); Elizabeth J. Jenkins, Springboro, OH (US); Robert F. Ondera, Casstown, OH (US)

(73) Assignee: UES, INC., Dayton, OH (US)

( * ) Notice: Subject to any disclaimer, the term of this patent is extended or adjusted under 35 U.S.C. 154(b) by 258 days.

(21) Appl. No.: 15/343,903

(22) Filed: Nov. 4, 2016

(65) Prior Publication Data

US 2017/0074755 A1    Mar. 16, 2017

Related U.S. Application Data

(63) Continuation-in-part of application No. 14/076,549, filed on Nov. 11, 2013, now Pat. No. 9,528,915.
(Continued)

(51) Int. Cl.
*G01N 1/06* (2006.01)
*G01N 1/32* (2006.01)
(Continued)

(52) U.S. Cl.
CPC .............. *G01N 1/06* (2013.01); *G01N 1/04* (2013.01); *G01N 1/286* (2013.01); *G01N 1/32* (2013.01);
(Continued)

(58) Field of Classification Search
CPC ............ G01N 1/06; G01N 1/04; G01N 1/286; G01N 1/32; G01N 1/36; G01N 23/04;
(Continued)

(56) References Cited

U.S. PATENT DOCUMENTS

| 4,143,544 | A | 3/1979 | DeVries et al. |
| 4,413,510 | A | 11/1983 | McCusker et al. |

(Continued)

FOREIGN PATENT DOCUMENTS

| CN | 1715886 | 1/2006 |
| CN | 202433293 | 9/2012 |

(Continued)

OTHER PUBLICATIONS

PCT, International Search Report and Written Opinion of the International Searching Authority, International Application No. PCT/US2017/059820, 16 pages, dated May 11, 2018.
(Continued)

*Primary Examiner* — Peter J Macchiarolo
*Assistant Examiner* — Irving A Campbell
(74) *Attorney, Agent, or Firm* — Thompson Hine LLP

(57) ABSTRACT

An metallographic system comprising a programmable controller, a robotic arm, a specimen clamping or holding device, a sectioning saw, a mounting station, a polishing station, a specimen preparation station, and an analyzer for examining the specimen.

16 Claims, 28 Drawing Sheets

Related U.S. Application Data

(60) Provisional application No. 61/725,786, filed on Nov. 13, 2012.

(51) Int. Cl.

| | |
|---|---|
| *G01N 1/36* | (2006.01) |
| *G01N 1/28* | (2006.01) |
| *G01N 1/04* | (2006.01) |
| *G06T 7/00* | (2017.01) |
| G01N 23/203 | (2006.01) |
| G01N 23/04 | (2018.01) |

(52) U.S. Cl.
CPC .............. *G01N 1/36* (2013.01); *G06T 7/0004* (2013.01); *G01N 23/04* (2013.01); *G01N 23/203* (2013.01); *G01N 2001/2873* (2013.01); *G01N 2223/61* (2013.01); *G06T 2207/10061* (2013.01); *G06T 2207/20016* (2013.01); *G06T 2207/20064* (2013.01); *G06T 2207/30156* (2013.01)

(58) Field of Classification Search
CPC ......... G01N 23/203; G01N 2001/2873; G01N 2223/61; G06T 7/0004; G06T 2207/10061; G06T 2207/20016; G06T 2207/20064; G06T 2207/30156
USPC ............................................... 73/104, 863.01
See application file for complete search history.

(56) References Cited

U.S. PATENT DOCUMENTS

| | | | |
|---|---|---|---|
| 4,655,700 | A | 4/1987 | Ahmed |
| 4,721,877 | A | 1/1988 | Kawakatsu et al. |
| 5,069,365 | A | 12/1991 | Woodhouse |
| 6,199,279 | B1 | 3/2001 | Humphrey et al. |
| 6,533,641 | B1 | 3/2003 | Morken et al. |
| 7,317,964 | B1 | 1/2008 | Spowart et al. |
| 7,319,914 | B1 | 1/2008 | Spowart et al. |
| 7,319,915 | B1 | 1/2008 | Spowart et al. |
| 7,319,916 | B1 | 1/2008 | Spowart et al. |
| 9,233,453 | B1 * | 1/2016 | Samuels ................... B24B 7/22 |
| 9,274,035 | B2 | 1/2016 | Hanswillemenke et al. |
| 2004/0266015 | A1 | 12/2004 | Favazzi et al. |
| 2006/0260414 | A1 | 11/2006 | Platzek |
| 2007/0160967 | A1 | 7/2007 | Halley |
| 2007/0231208 | A1 | 10/2007 | Tanaka et al. |
| 2008/0003446 | A1 | 1/2008 | Furukawa et al. |
| 2008/0202920 | A1 | 8/2008 | Iwaya et al. |
| 2009/0088047 | A1 * | 4/2009 | Zurbuchen .............. B24B 49/12 451/6 |
| 2009/0308174 | A1 | 12/2009 | Cutshall |
| 2010/0276578 | A1 | 11/2010 | Shelley et al. |
| 2011/0168693 | A1 | 7/2011 | Rudd et al. |
| 2014/0086808 | A1 | 3/2014 | Itoh |
| 2014/0130613 | A1 | 5/2014 | Adiga et al. |
| 2014/0157914 | A1 | 6/2014 | Fischione et al. |
| 2016/0231211 | A1 | 8/2016 | Liu et al. |

FOREIGN PATENT DOCUMENTS

| | | |
|---|---|---|
| CN | 203732342 | 7/2014 |
| CN | 204008252 U | 12/2014 |
| CN | 204177661 | 2/2015 |
| CN | 204487355 | 7/2015 |
| CN | 205201305 | 5/2016 |
| CN | 205271727 | 6/2016 |
| CN | 105965350 | 9/2016 |

OTHER PUBLICATIONS

PCT, International Search Report and Written Opinion, PCT/US2013/069852 (dated Apr. 4, 2014).
ASM (American Society for Metals) Handbook, Metals Handbook® Ninth Edition Volume 9 Metallography and Microstructures, chapter entitled "Sectioning," pp. 23-32 (1985).
Russ, J.C., The Image Processing Handbook, Fourth Edition, CRC Press, Chapter 8—Global Image Measurements (40 pages) (2002).
Aubert, G. et al., Mathematical Problems in ImageProcessing: Partial Differential Equations and the Calculus of Variations, Springer, New York, Chapter 4—The Segmentation Problem, pp. 137-187 (2000).
Aubert, G. et al., Mathmatical Problems in Image Processing: Partial Differential Equations and the Calculus of Variations, Springer, New York, Chapter 5—Other Challenging Applications, pp. 189-225 (2000).
Adiga, U.P.S., "Integrated Approach for Segmentation of 3-D Confocal Images of a Tissue Specimen," Microscopy Research and Techniques, vol. 54, pp. 260-270. (2001).
Adiga, U.P.S. et al., "An Efficient Method Based on Watershed and Rule Based Merging for Segmentation of 3-D Histopathological Images," Pattern Recognition, vol. 34, pp. 1449-1458 (2001).
Laptev, I. et al., "Tracking of Multi-State Hand Models Using Particle Filtering and a Hierarchy of Multi-Scale Features,"M. Kerkhove (Ed.), Scale-Space, LNCS 2106, pp. 63-74 (2001).
Rizon, M. et al., "Object Detection Using Geometric Invariant Moment," American Journal of Applied Sciences, vol. 2, No. 6, pp. 1876-1878 (2006).
Haralick, R.M., "Statistical and Structural Approaches to Texture," Proc. of the IEEE, vol. 67, No. 5, pp. 786-804 (May 1979).
Pietikäinen, M., "Image Analysis with Local Binary Patterns," Image Analysis: Lecture Notes in Computer Science, vol. 3540, pp. 115-118 (2005).
Bashar, M.K. et al., "Image Retrieval by Local Contrast Patterns and Color," Bebis et al. (Eds.), ISVC, LNCS 4292, Springer-Verlag Berlin Heidelberg, pp. 136-145 (2006).
Kruskal, J.B., "Multidimensional Scaling by Optimizing Goodness of Fit to a Nonmetric Hypothesis," Psychometrika, vol. 29, No. 1, pp. 1-27 (Mar. 1964).
Uchic, M.D., "Serial Sectioning Methods for Generating 3d Characterization Data of Grain- and Precipitate-Scale Microstructures " *Computational Methods for Microstructure-Property Relationship, Ghosh, S., Dimiduk, D. (Eds.)*, pp. 31-52 (2011).
Product Information featuring "A Fully Automated, Serial Sectioning System for Three-Dimensional Microstructural Investigations" Robo-Met.3D®, A UES Product (2012).
Webpage featuring "Robo-Met.3D®, A Fully Automated, Serial Sectioning System for Three-Dimensional Microstructural Investigations" by UES, http://www.ues.com/content/robomet3d (2014).
Schorr et al. "Characterization of Thermal Spray Coatings", Materials Characterization, pp. 93-100 (Nov. 15, 1999) www.sciencedirect.com/science/article/pii/S1044580398000485/pdfft?md5=84056c29438ae89b6711ca7ef8d92894&pid=1-s2.0-S1044580398000485-main.pdf.
EP, Supplementary Search Report, European Application No. 13854764.1 (dated Jun. 24, 2016).
U.S., Non-Final Office Action; U.S. Appl. No. 14/076,549 (dated Sep. 24, 2015).
U.S., Final Office Action; U.S. Appl. No. 14/076,549 (dated Apr. 4, 2016).
U.S., Notice of Allowance; U.S. Appl. No. 14/076,549 (dated Jul. 27, 2016).

\* cited by examiner

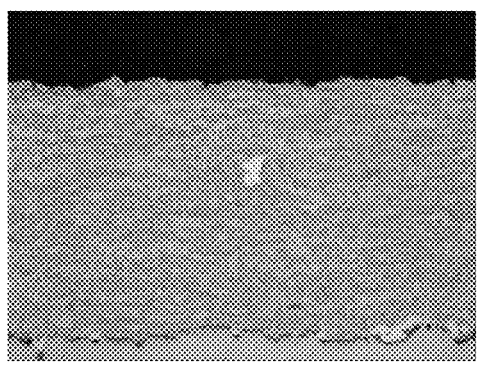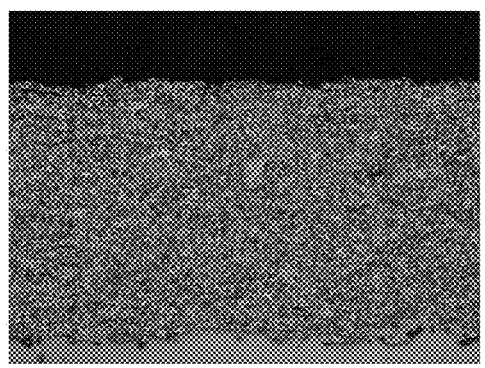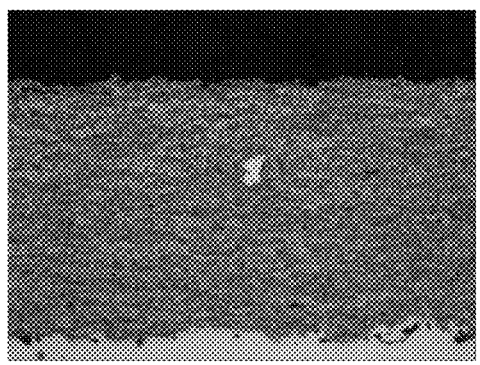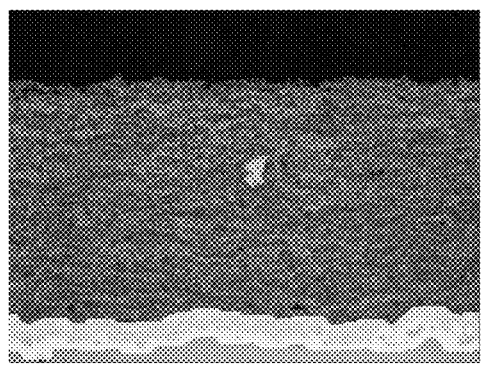
FIG. 12

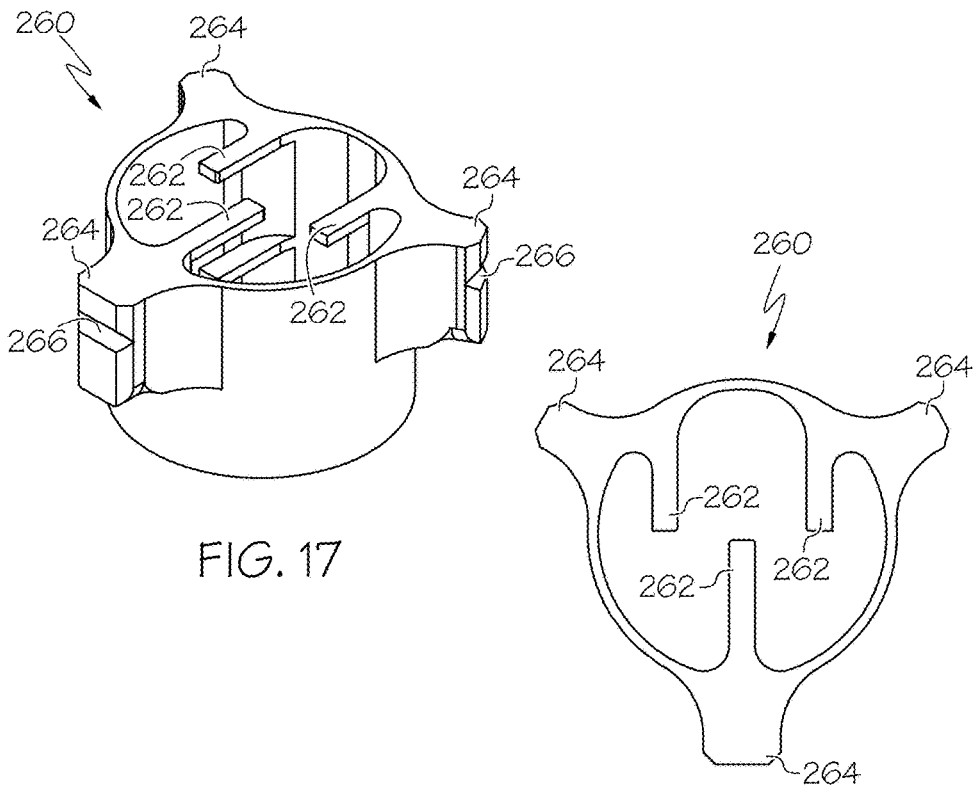
FIG. 17
FIG. 18
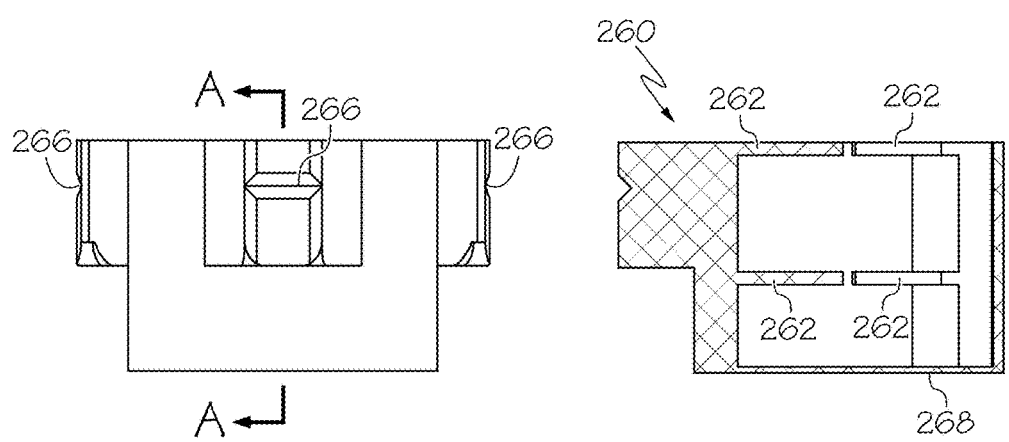
FIG. 19
FIG. 20

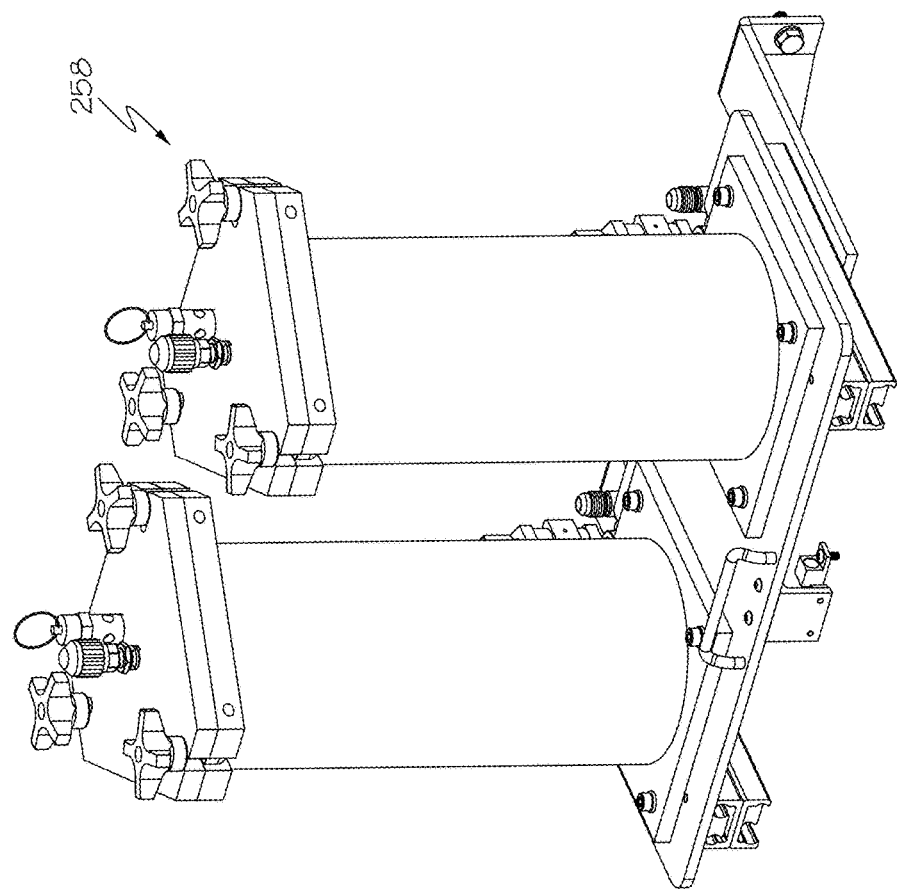

AUTOMATED HIGH SPEED METALLOGRAPHIC SYSTEM

PRIORITY CLAIM

This application is a continuation-in-part of U.S. application Ser. No. 14/076,549, filed Nov. 11, 2013, and claims priority from U.S. Provisional Application 61/725,786 filed Nov. 13, 2012.

GOVERNMENT LICENSE RIGHTS

This invention was made with government support under Contract Number FA8750-12C-0197 awarded by the United States Air Force. The government has certain rights in the invention.

BACKGROUND

Herein is described an automated industrial metallography (AIM) system that provides several advantages over existing equipment and methods. The automation of metallography significantly improves the efficiency and consistency of specimen processing, by eliminating the subjective nature of preparation and image analysis. The system and method described herein enable the automated performance of QA/QC for materials science. Specific advantages of each feature will be described in greater detail below.

The AIM System will enable the rapid evaluation of coatings applied to various components and eliminate the need for human intervention in assigning a pass/fail grade. The disclosed system will give the process engineer precise control over all metallographic preparation parameters including mounting, sectioning, polishing, cleaning, and imaging. It will provide high speed, real time, repeatable and accurate data, improving the confidence in depot repairs, and eliminating the need for manual preparation and analysis. Pass/fail results for coatings can be obtained without human intervention. In one embodiment, the system may be used to evaluate high-velocity oxygen fuel (HVOF) thermal spray Tungsten Carbide Cobalt (W—C—Co) coating.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 12 depicts a series of photographs of the interface between the coating 55 shown in FIG. 1A and the base or substrate at the location of the cut face in the test specimen.

FIG. 17 is a perspective view of a specimen mounting cup.

FIG. 18 is a top view of the specimen mounting cup of FIG. 17.

FIG. 19 is a side view of the specimen mounting cup of FIG. 17.

FIG. 20 is a cross-section view through line A-A of FIG. 19.

FIG. 24A is a perspective view of a resin reservoir.

DETAILED DESCRIPTION

U.S. Pat. Nos. 7,319,914, 7,319,915; 7,319,964; and 7,319,916 are incorporated herein in their entirety by reference including, but not limited to, their description of the components of the automated metallographic system such as sample preparation, serial sectioning, polishing, cleaning, etching, imaging, image acquisition, and microstructural analysis of materials, and related hardware control software routines as disclosed therein.

Specimen analysis will proceed as follows in one embodiment: A technician will place a coated sample (sometimes referred to as a "coupon") in a sample carousel of the AIM system. A robotic arm will grip the coupon and transfer it to a precision sectioning saw where it will be placed on a stage for cutting. Once the coupon has been cut, a second robotic arm will transfer the coupon to a polishing unit where the cut face of the coupon will be polished in conformance with industrial standards. The sample will then be transferred to a cleaning station where in one embodiment, the sample may be subjected to a three stage cleaning process. The prepared sample in one embodiment, will then be subjected to an image acquisition process wherein the images collected will be subjected to image processing algorithms adapted specifically for the AIM system to evaluate the quality of coating and make a pass/fail determination, thereby eliminating the subjectivity and inconsistency of the decision. This determination based upon an artificial intelligence (AI) classification algorithm which may employ machine learning to enhance accuracy. See References 2 and 3 below which are incorporated herein in their entirety by reference.

Figure 1:
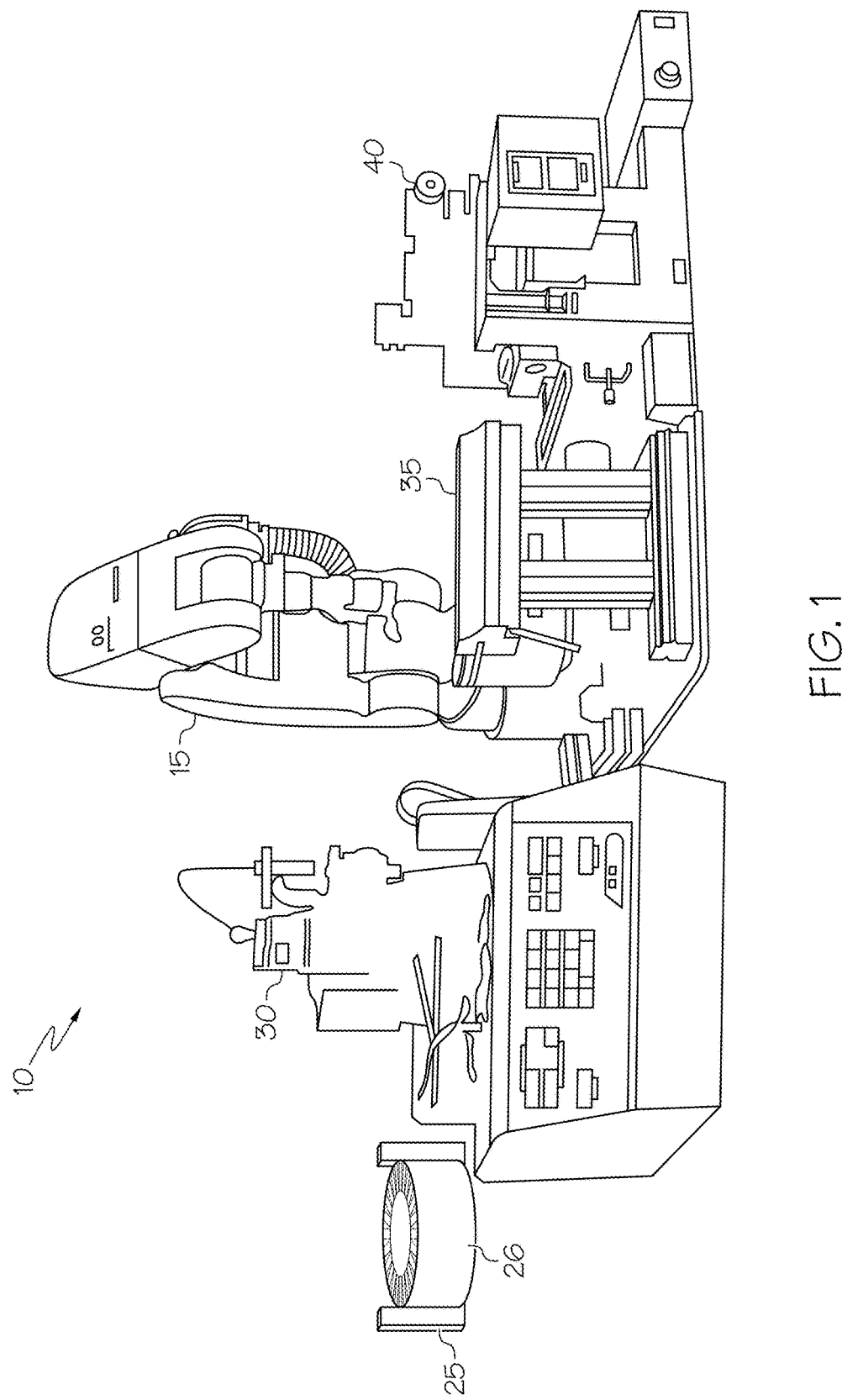
FIG. 1 depicts an Automated Industrial Metallography (AIM) System according to one or more embodiments shown and described herein.
Figure 1A:
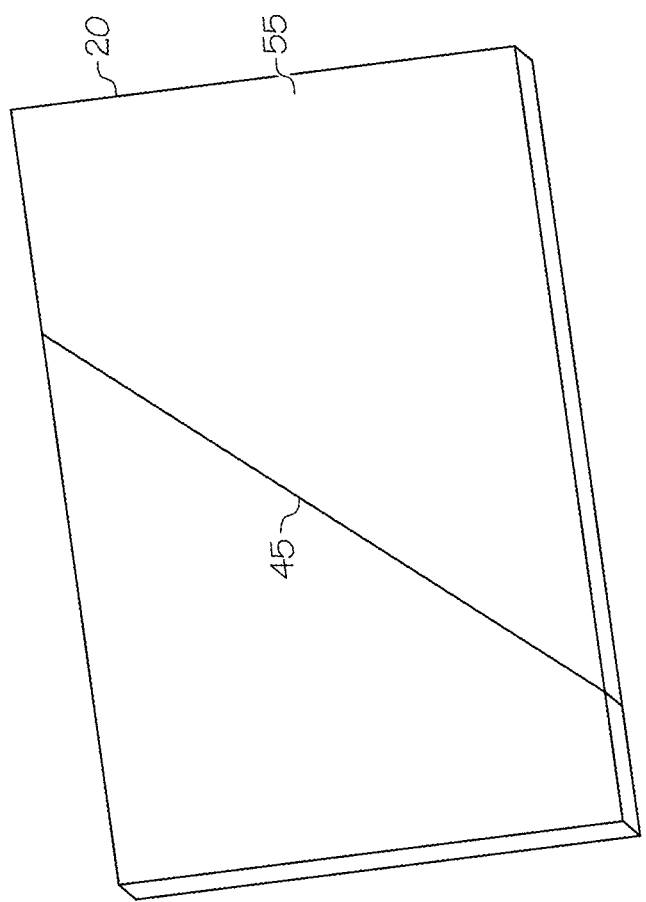
FIG. 1A depicts a coated specimen. The angular line 45 on the surface of the specimen indicates the position of a cross-cut for sample analysis as described herein.
Figure 3:
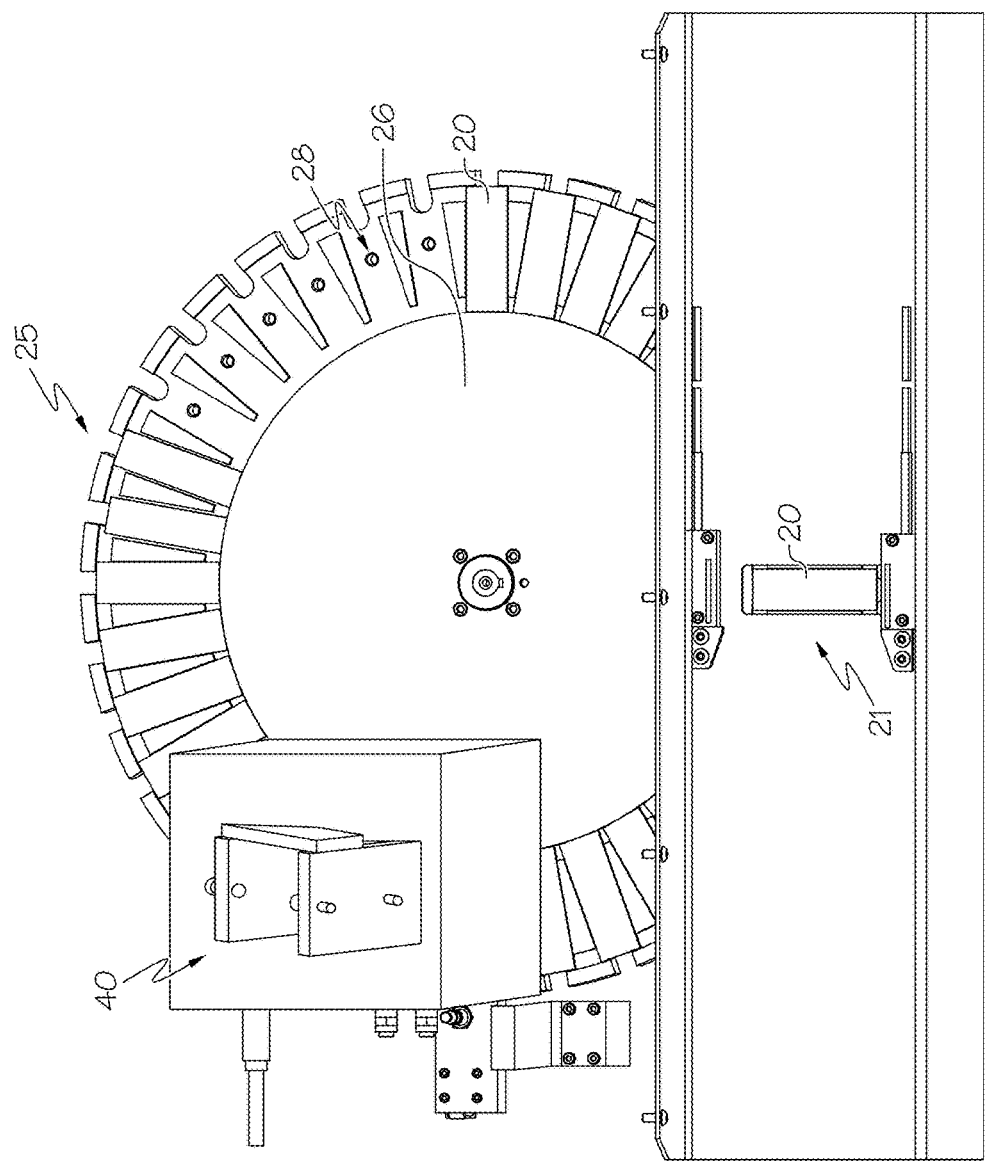
FIG. 3 depicts an overhead view of a turn table or carousel for loading multiple coupons or specimens for transfer into the system.

Referring to FIG. 1, the basic components of one embodiment of the AIM system 10 are depicted. In the depicted embodiment, the robotic arm 15 is configured to move the specimen 20, as shown in FIG. 1A, from a specimen loading and delivery device 25, a specimen preparation station 35, to a polishing station 30, and a microscope or other analytical instrument for sample evaluation. The specimen holding device 25 is illustrated in FIG. 3. The holding device 25, in one embodiment includes a slotted carousel 26 that receives, transports and labels the samples. The carousel 26 delivers each specimen or coupon 20 to a pen stamp 40 where it is labeled, enabling tracking throughout the analysis process. The technician manually or robotically places the specimen on a loading area 21 in the specimen holding device 25. The loading area 21 includes one or more and preferably an array of optical sensors for verifying that the specimen has been placed at the loading position and is available and ready for analysis. In one embodiment, the sensors may be arranged in an array so that the system can verify that an object has been placed on the loading position and the object is in fact a specimen. Once the specimen 20 is verified it is captured in one of the radial slots 28 in the carousel 26. In some embodiments, the system 10 may ask for specimen or coupon information such as lot number, coating type, time and date of application, application technician, temperature, and position in the specimen holding device 25 for example before removing the specimen 20 from the carousel 26. When the system 10 has completed gathering specimen information, the robotic arm 15 or a separate robotic arm removes the specimen 20 from the specimen carousel 26 and starts the preparation and examination process.

In one embodiment, the preparation station 50 includes a sectioning saw 52 to cut the specimen to expose a cross-section of a coating 55 on the surface of the specimen 20. Alternatively, the specimen may be grinded to obtain the cross-sectional cut. FIG. 1A depicts the specimen 20 with the cross-sectional cut indicted by a line 45. The coating 55 applied to a surface of the specimen 20 may be a thermal spray coating, paint, epoxy, glass, or any other coating that may be applied to a surface for analysis as described herein. The specimen (base) 20 may be wood, ceramic, composite, metal, plastic, organic or biological material, etc.

Figure 2:
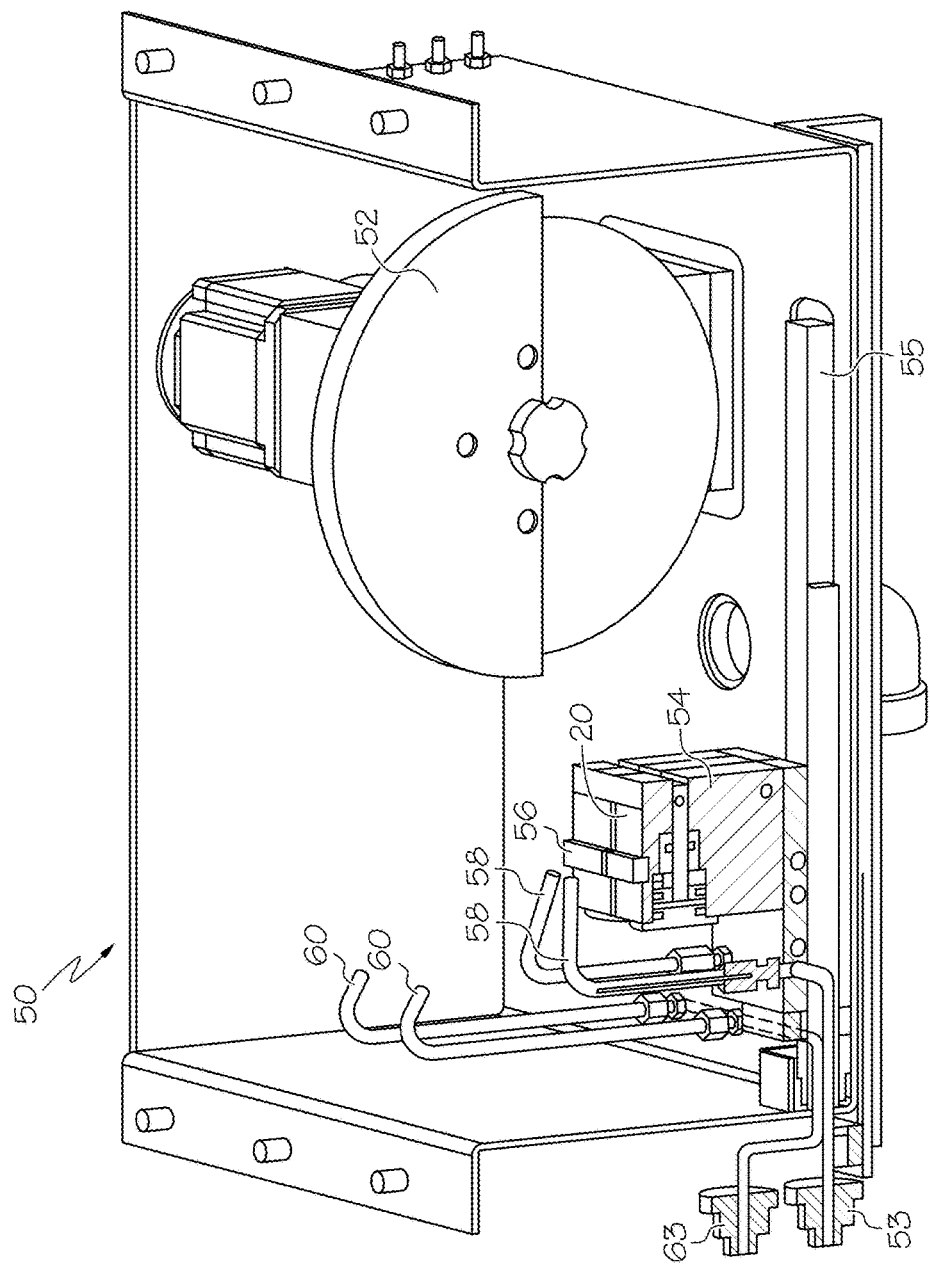
FIG. 2 depicts an overhead perspective view of a cutting module for cross-cutting a specimen according to one or more embodiments shown and described herein.

The specimen 20 may be placed on a stage 54 by the robotic arm 15 where it is retained by gripping elements 56 for cutting by a robotic arm in one embodiment of the invention shown in FIG. 2. This arm may be designed to move the specimen from the carousel 26 to the stage 54 for cutting and then to the polishing platen. The specimen may be held in position during cutting by a specialized gripper or vice 56 that anticipates the cutting location based on the designated material test standards for each coupon. A coolant spray may be used to cool the blade of the sectioning saw, cool the specimen, and remove debris. The sectioning saw may be a high precision sectioning machine, such as TechCut 5™ made by Allied High Tech products, which is programmable and designed to cut a wide variety of materials, but similar cutting tools may be used. The sectioning saw may be communicatively coupled to a microprocessor unit that will control sample feed rate, distance and force, and will automatically adjust feed rate as the cutting condition changes due to varying thickness and/or material differences in the specimen. When sectioning is complete, the stage 54 will automatically retract the specimen along the rail member 55 to the home position and stop saw blade rotation and coolant spraying. In the shown embodiment the specimen is sprayed with water through nozzles 58 as it is cut. To dry the specimen, air is sprayed through tubes 60 which respectively inject air into the cross cutting device. Water and air are introduced via ports 53 and 63 into the cutting compartment 50.

Figure 5:
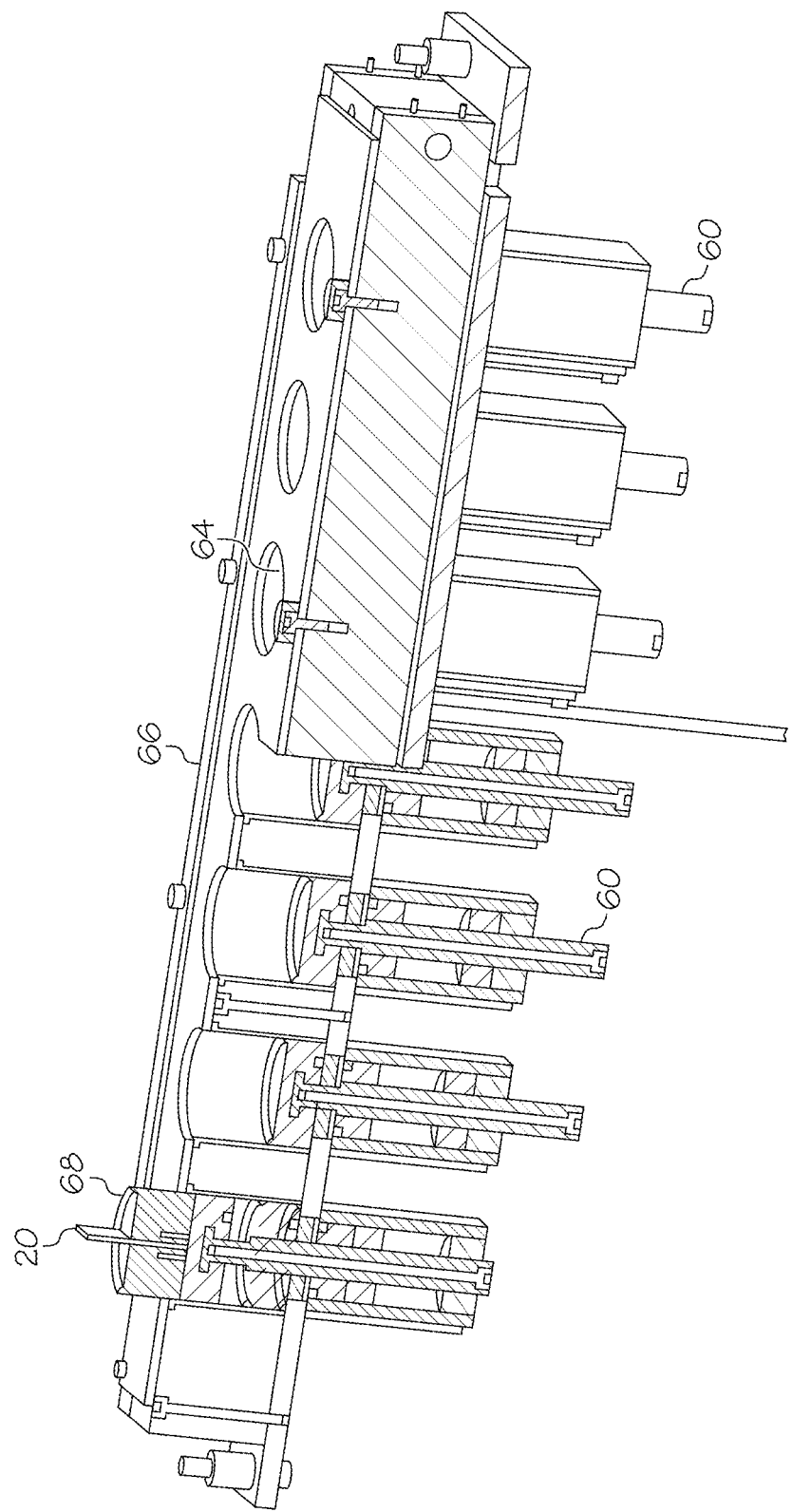
FIG. 5 depicts an expandable automated multiple sample mounting and delivery system in which a piston is used to eject the mounted sample from a mold according to one or more embodiments shown and described herein.
Figure 7:
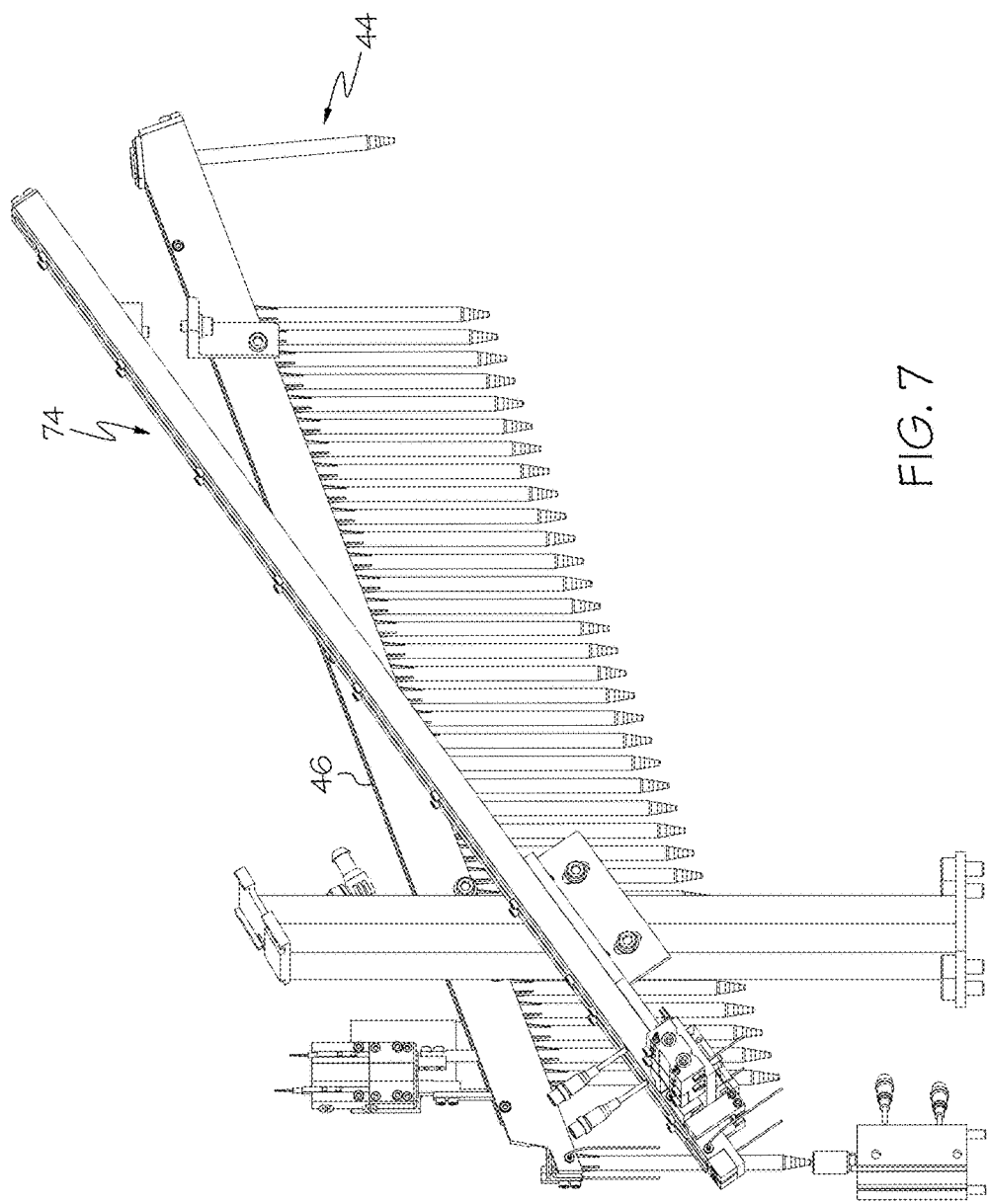
FIG. 7 depicts an automated system for supplying clips and injection nozzles to the robotic arm for use as described herein.

The specimen mounting device 35 automates the mounting process by simultaneously mixing and dispersing a cement such as a 2-part epoxy from supply tanks that reside inside the canister 42. The cup 25 collects any resin drips. The epoxy is mixed in a mixing head 48. The robotic arm attaches a nozzle 44 that it picks up from the nozzle supply device 46 that is shown in detail in FIG. 7. The nozzles 44 are grasped by the robotic arm 15 and assembled with the dispenser 48. The mixing head 48 reciprocates from the resin supply canister 42 to a mold tray 66 where it dispenses the resin into a mold 64 that is best seen in FIG. 5. Epoxy setting and curing may be accelerated by controlling the temperature of the mounting device.

Figure 4:
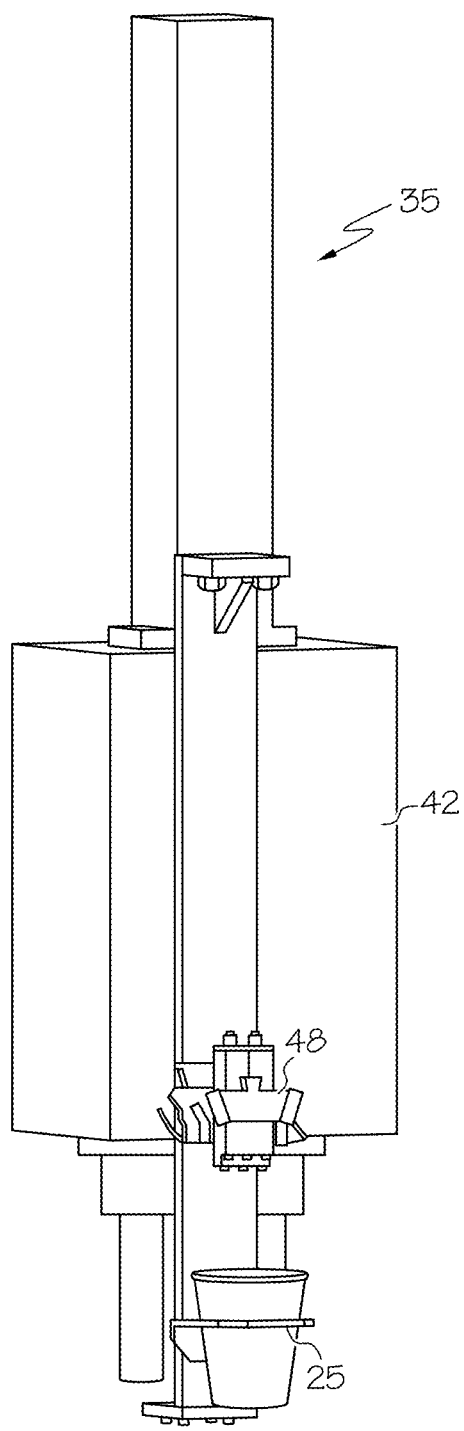
FIG. 4 depicts an automated disposable mount material injector system.
Figure 6:
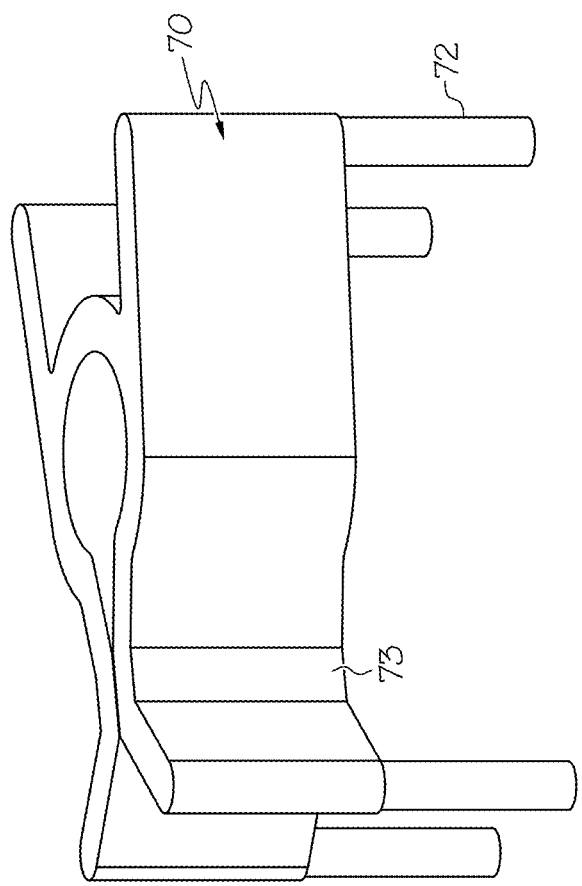
FIG. 6 depicts a clip that positions the specimen in a mold for mounting.

The inside surface of the mold may be lubricated with an oil, grease or the like to facilitate removal of the mounted specimen as described next. The specimen 20 is assembled with a support or mounting clip 70 that includes a living hinge 73 such that by grasping and squeezing the hinge, the clip can become attached to the specimen 20. One example of a clip is shown in FIG. 6 and includes a plurality of legs 72 that support the specimen as it stands in the resin in the mold 64. The clips 70 are dispensed from a magazine 74 as seen in FIG. 4C. After the mold is filled with the resin, the specimen 20 with the attached clip 70 is placed in the resin in the mold. After the resin sets, a piston 60 as shown in FIG. 5 may be used to expel the mounted specimen 68 from the mold after the resin sets. Alternatively, the polishing station may include a clamping device to provide for easy specimen manipulation and to preserve sample integrity during the preparation and imaging processes.

Figure 9:
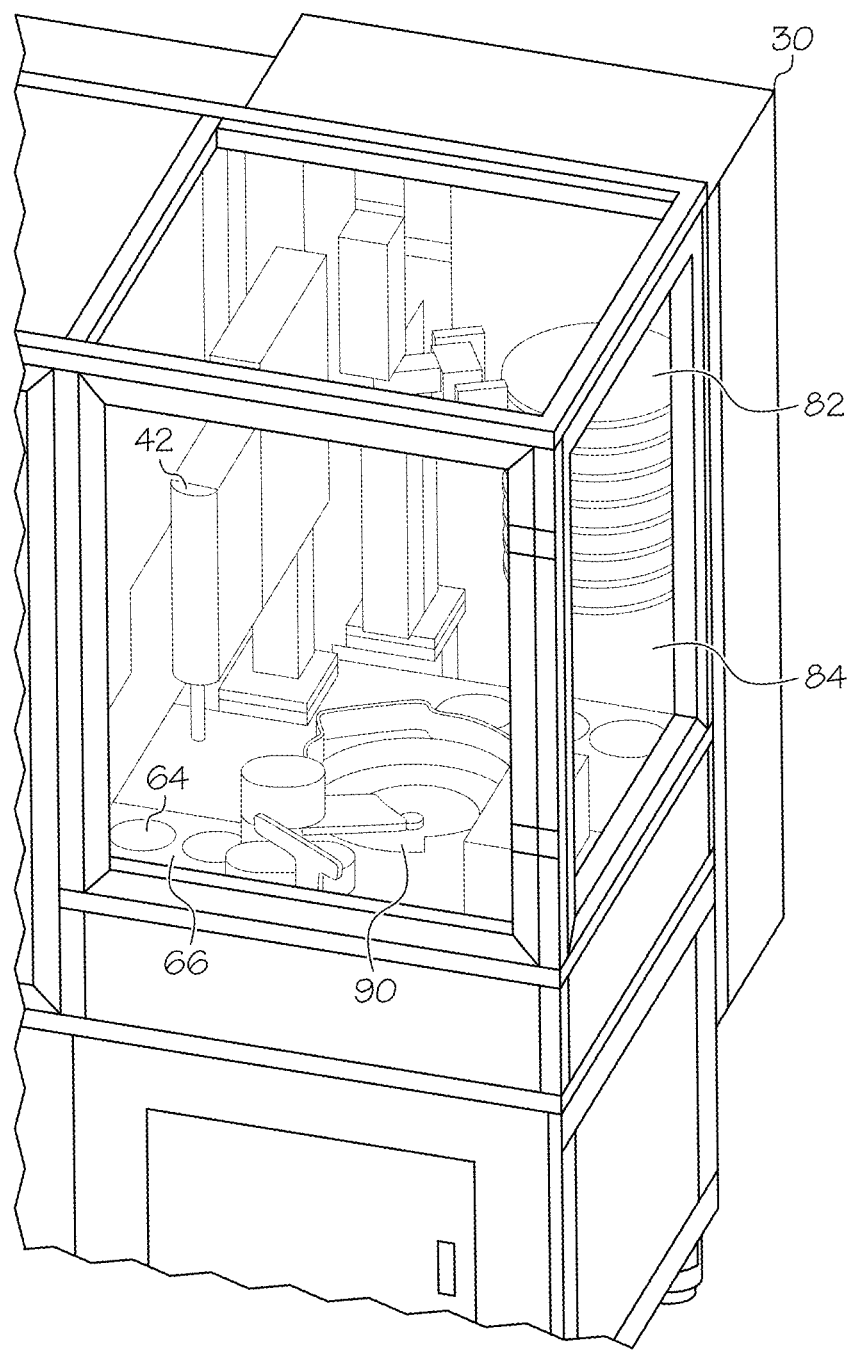

In one embodiment as shown in FIG. 9, the polishing station includes a plurality of polishing heads in the form of platens 82. A polishing head 82 may be used to polish the specimen and the face of the cross-sectional cut 45. The polishing head 82 may be covered by an abrasive-impregnated polishing medium that may include by example and without limitation, a cloth or a film. The polishing station 30 may also use an abrasive polishing media to include without limitation, an abrasive slurry, sandpaper, polishing stone, etc. In some embodiments, the polishing station 30 may also include a wiping cloth (not shown) to collect and remove any material displaced by the polishing station 30. The specimen 20 may be coated with a lubricant to prevent scratching by the wiping cloth and collected material during wiping.

In one embodiment, the polishing station 30 may have a multi platen cassette holder 84 in which are mounted platens 82 which are coated with an abrasive calibrated using industry standard methods to produce a near perfect planar polishing surface. An abrasive media can also be applied to the abrasive surface of the platen.

Some embodiments may employ the robotic arm 15 in polishing the resin mounted specimen 68. The robot is capable of creating sample rotation (0 to 180 degrees) as well as sample sweep to give robust yet controlled material removal rate. The rotating mechanism may be able to rotate between 0 to 360 degrees as well as sweep the specimen 20 in an x-y axis perpendicular to the polishing head to control a polishing rate and provide the ability to remove only minute amounts of material from the surface 55 of the specimen 20.

A dispenser may be used to dispense the polishing media. In one embodiment a peristaltic pump may be used to dispense any of the multiple abrasive media suspensions that may be provided onto the abrasive surface of the platen 82. Each dispenser is connected to a flow regulator that gives precise control over abrasive solution dispensing. Without limitation, the dispenser may dispense polishing media or abrasive solutions that may include, without limitation, diamond suspension, colloidal silica, alumina, and other abrasive solutions. The solutions are user-defined and the system is programmable such that they may be changed at any interval. Furthermore, the polishing media may be changed during the polishing process and/or several types of polishing media may be used during the polishing process.

In some embodiments, polishing station 30 may perform a rough polish and a fine polish. The rough polishing may be used to remove any deformation produced by the sectioning saw and/or grinding process. The polishing head may be fitted with a diamond abrasive ranging from 9 to 1 micron. The specimen 20 may be wiped with a polishing cloth that will hold relief and undercutting interference to a minimum.

The hardness of the specimen 20 and/or of the coating will determine the type of cloth to use. Proper rough polishing maintains specimen planarity and retains all inclusions or secondary phases. Rough polishing is primarily associated with diamond abrasives ranging from 9 to 1 micron. The type of cloth used for this stage of the process has a bearing on the end result. It is imperative that relief between microconstituents of varying hardness and sample mount interfaces be held to a minimum. Napless cloths will hold relief and undercutting at interfaces to a minimum. The hardness of the material being prepared should be used as a guide to selecting the cloth in this stage.

The fine polishing may remove any deformations that result from the rough polishing. The type of specimen 20 material, the chemical cleaning and optical conditions of the examination will determine the type of polishing agent and/or polishing medium used. A uniformly polished and scratch free surface is desired. Attaining this will depend on the specimen material (more difficult with soft materials), the etching conditions (more difficult with etchants that are sensitive to deformed structures), and the optical conditions of the examination. In general, high-standard polishing processes are more laborious and require greater operator skill. Napped cloths are generally preferred for this stage of the process with diamond suspensions ranging from 1 to 0.03 microns. In one embodiment, a polishing medium with a diamond suspension may be used with an abrasive range between 45 to 0.03 microns.

In certain alternative embodiments, polishing may be performed by plasma, laser, or electropolishing devices instead of by using the abrasive platens.

The system is equipped to clean the polished specimen. In the embodiment illustrated cleaning is carried out in the central area 90 of the cabinet housing the polishing station 30. In one embodiment, the cleaning may include sample rinsing, two-stage ultrasonic cleaning and an alcohol immersion, followed by drying of the sample. In some embodiments, the chemical cleaning may be automated to remove the human error often associated with etching. In one embodiment the system 10 may be equipped with three chemical wells coupled to three separate chemical bottles via peristaltic pumps. The system will carry the resin mounted specimen 68 and immerse the specimen portion 20 in the designated chemical etching/cleaning well where an appropriate reagent is re-circulated.

Figure 8:
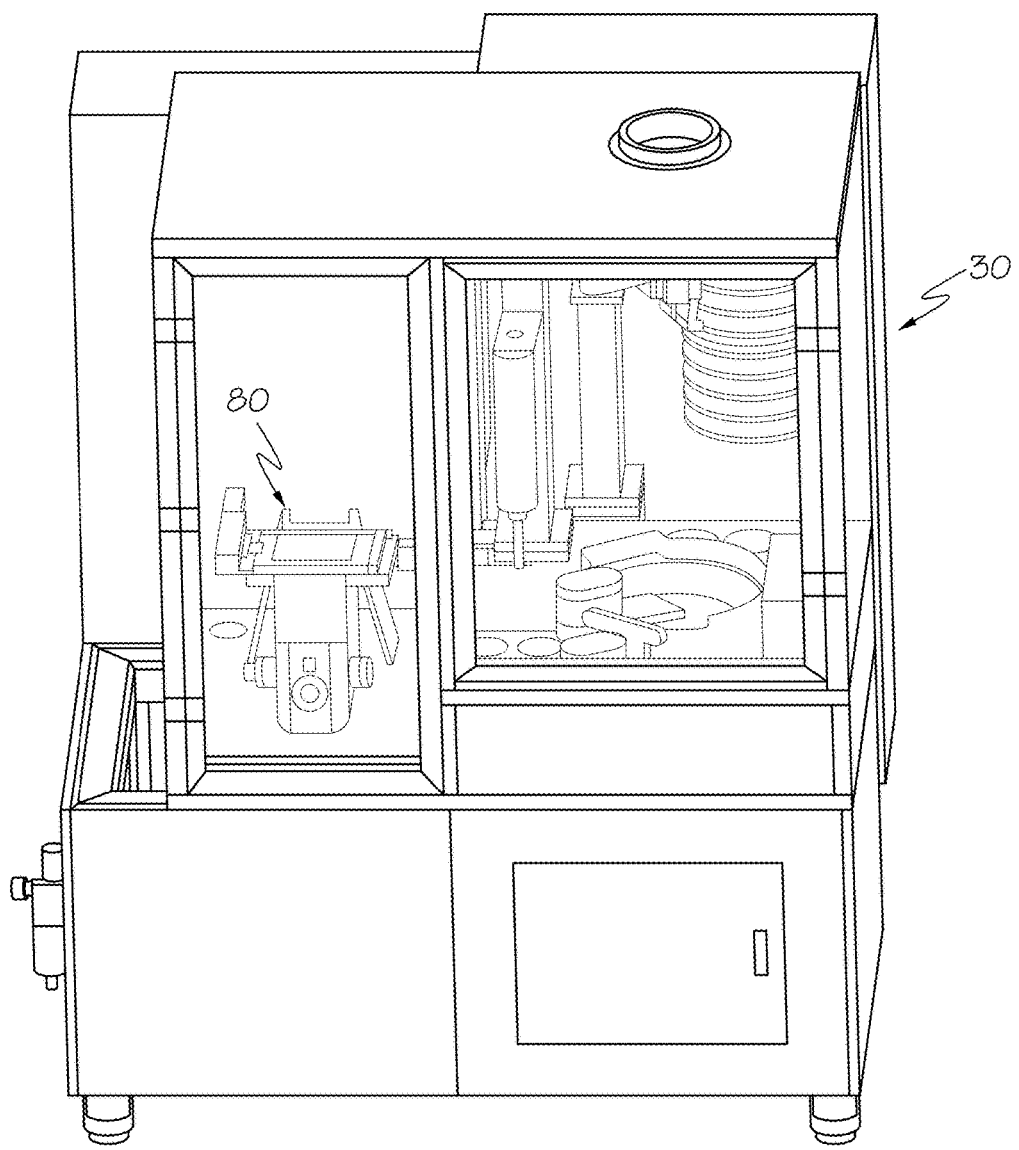
FIGS. 8 and 9 depict an apparatus for polishing the cut specimen, according to one or more embodiments shown and described herein. The system includes a software-controlled table of recipes that can be loaded to control the number and order of platens used, and the abrasive used based on the amount of polishing desired for each specimen.

The specimen preparation station 35 is used to prepare the specimen 20 for viewing in the automated microscope 40 (80 in FIG. 8). The specimen preparation station 35 may include facilities for washing and drying the specimen 20. The washing may include using a washing device that does not touch the specimen 20 with any cleaning apparatuses and use any type of washing fluid. In some embodiments, the specimen preparation station 35 may use an ultrasonic cleaner or the like and distilled water as the washing fluid. The specimen 20 may then be rinsed with any type of rinsing fluid, for example an alcohol product like isopropyl alcohol for example. The specimen 20 may be dried using a stream of compressed gas, for example nitrogen, air, or similar gases. The specimen 20 may also be dipped into a chemical cleaning solution to chemically clean the specimen 20 and the cross-sectional cut 45. The chemical cleaning solution, in one embodiment, may be or include an etchant. The etchant will subject the polished surface of specimen 20 to a chemical reaction. Etching will be followed by cleaning and drying of the specimen 20. Once the parameters are defined, the same cleaning routine is preferably followed for every similar specimen 20. In some embodiments, the cleaning of the specimen 20 may include a four stage process that may be repeated until the specimen 20 is ready for viewing and/or imaging. The four stage process may include rinsing, two-stage ultrasonic cleaning, alcohol immersion followed by drying.

In some embodiments, the system may include one or more polishers, microscopes, and/or sectioning saws.

In some embodiments, the system may incorporate hardness, tensile, bond strength and/or bend testing analytical capabilities.

Figure 1B:
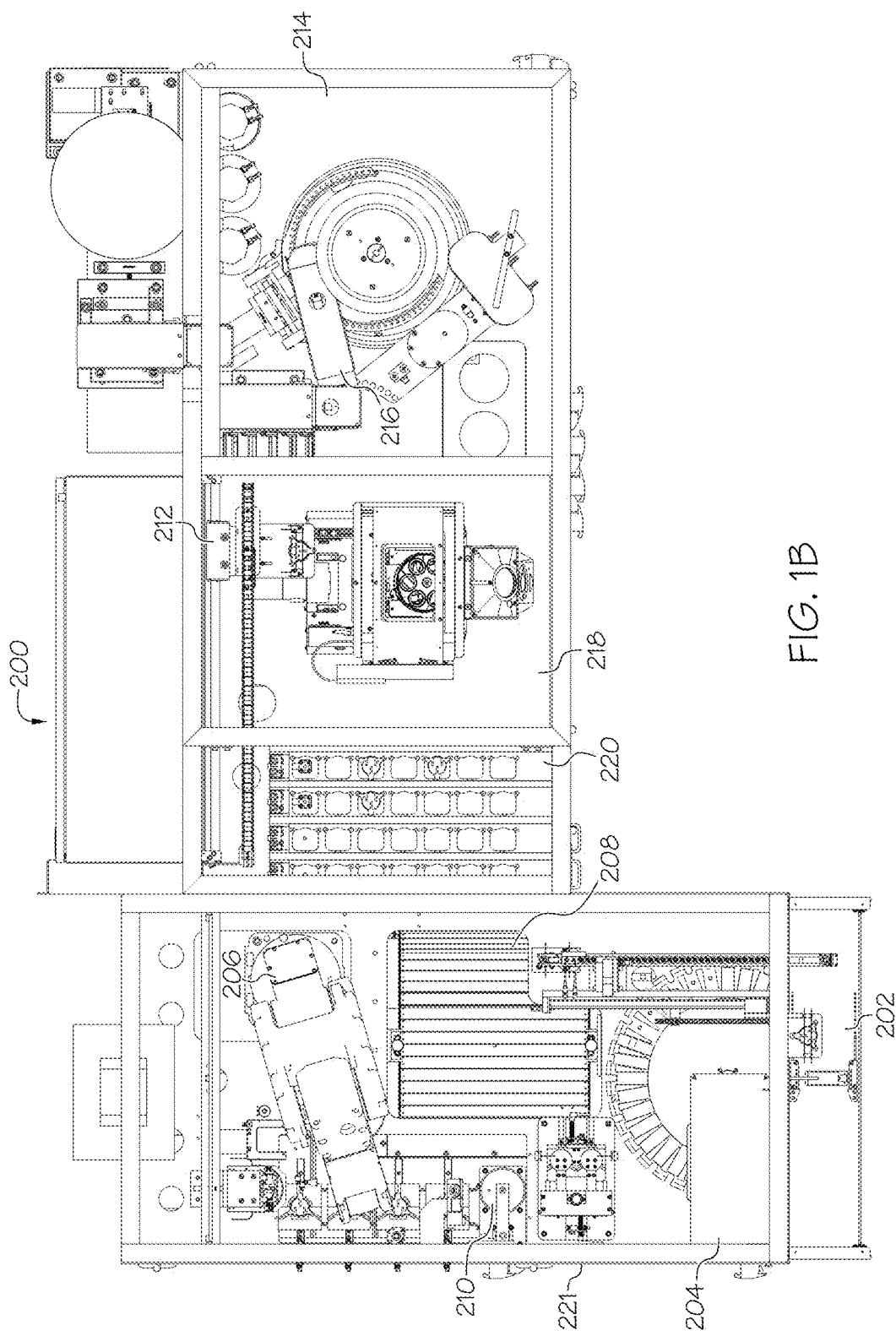
FIG. 1B is a top view of an automated metallographic system according to one or more embodiments shown and described herein.
Figure 1C:
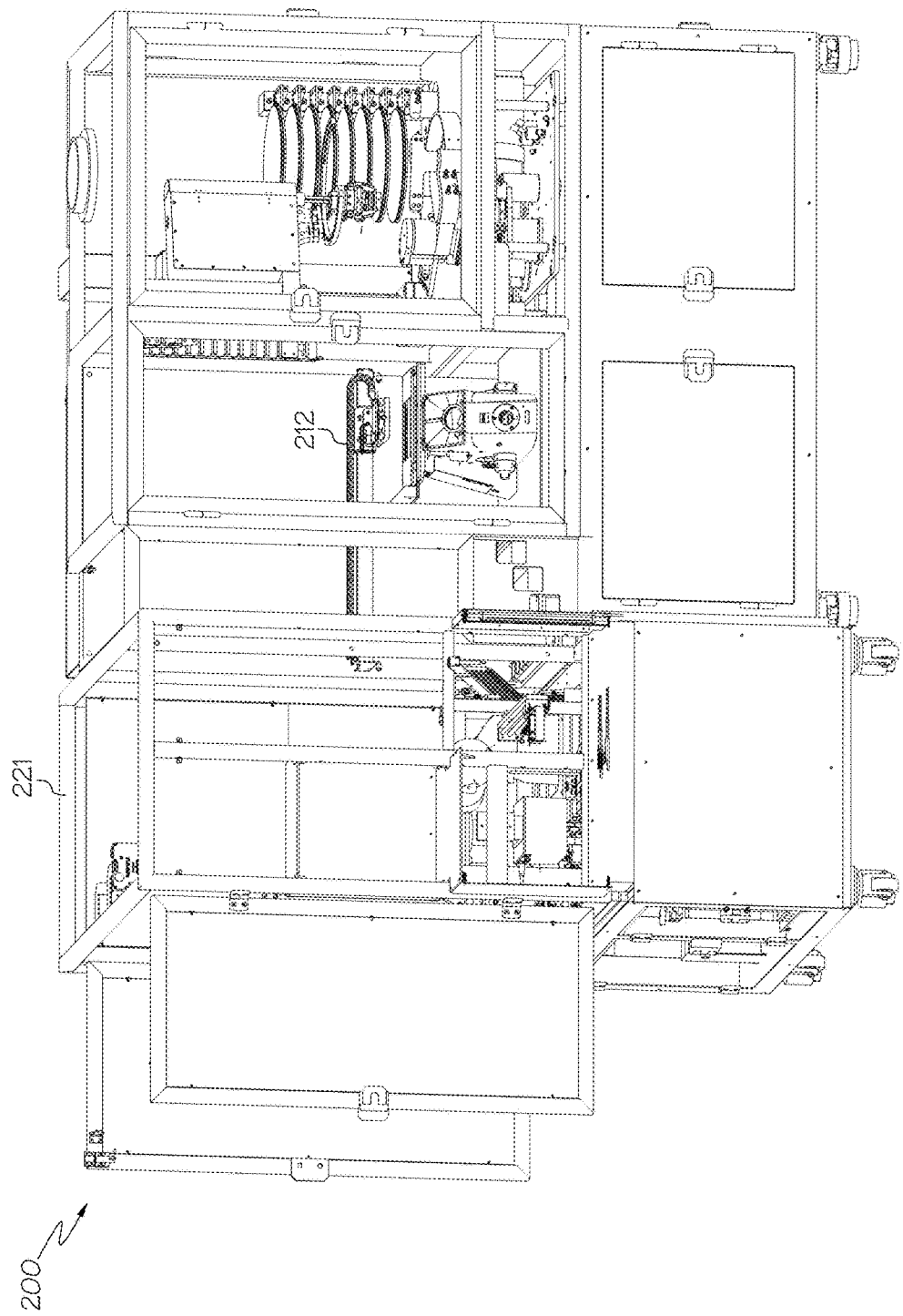
FIG. 1C is a front perspective view of the automated metallographic system of FIG. 1B.

Referring to FIG. 1B, the layout of another embodiment of an automated specimen preparation and analysis system 200 is shown. As will be described in more detail below, the automated metallographic system according to this embodiment has a specimen loading station 202, a specimen labeling station 204, a first robotic arm 206, a preparation station 208, a mounting station 210, a sample transportation rail 212, a grinding and polishing station 214, a second robotic arm 216, an imaging station 218, a sample storage area 220, and an outer housing 221. The outer housing 221 may substantially or completely surrounds at least the first robotic arm 206, the preparation station 208, and the mounting station 210 to protect lab personnel from moving parts. A controller, which may comprise one or more processors and one or more memory storage devices, is operatively connected to each of the stations, the robotic arms, and the transportation rail, and is configured to fully automate the system by executing stored instructions including, for example, instructions associated with a sample mounting routine.

Figure 21:
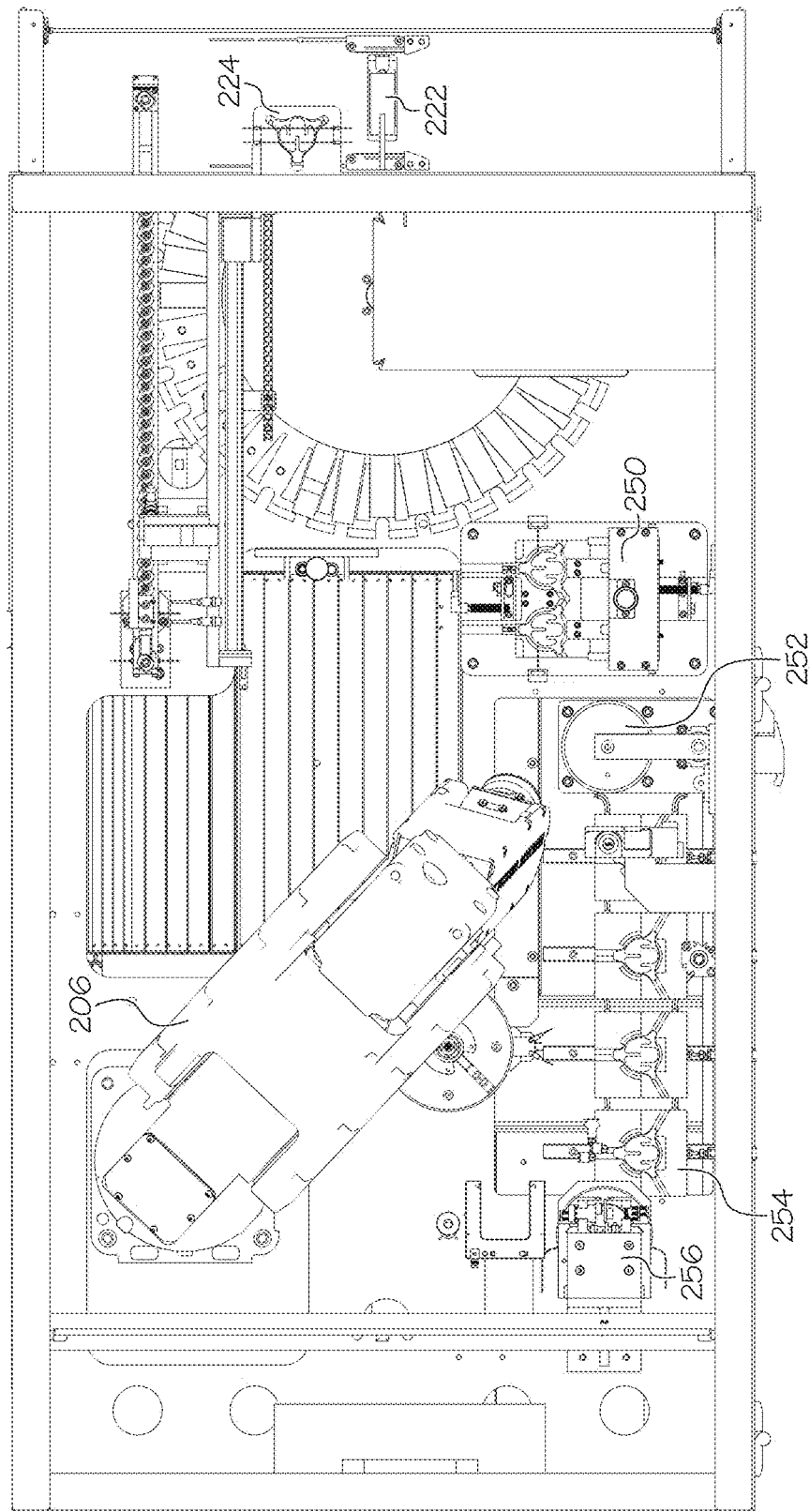
FIG. 21 is a close up top view of a portion of the system of FIG. 1B including a loading station, a preparation station and a mounting station.

The specimen loading station 202 may be provided on the front exterior of the system and includes at least one input opening through the outer housing 221 through which specimens can be loaded into the system. According to one embodiment the input opening is a specimen loading slot 222 where a technician can insert a standard coated sample—typically 1 inch by 3 inches. This slot is best seen in FIG. 21. To ensure proper orientation of the specimen during preparation and analysis, specimens may be loaded through the slot with the coating side face down. Alternatively, the system could be designed so that specimens are always loaded with the coating side up.

The loading station may also include a bypass input opening 224 where pre-mounted samples can be loaded into the system. Specifically, the bypass input opening 224 may include an input tray where specimens that have already been mounted in a specimen mounting cup can be inserted or reinserted into the system for additional or repeated analysis. In some instances, a specimen may already be positioned within a specimen mounting cup but not yet mounted within resin. In that case, the specimen mounting cup may be received and advanced directly to the mounting station 210 after bypassing the preparation station 208. In other instances, the specimen may already be fully mounted within resin. In that case, the specimen mounting cup may be received through the bypass input opening 224 and advanced to the polishing station 214 after bypassing the preparation station 208 and the mounting station 210. In still other instances, a specimen that has already undergone analysis may be reinserted into the system through the bypass input opening 224 and advanced directly to the analyzer or advanced out of order from previously loaded specimens.

One or more optical sensors may be used to verify that a specimen has been placed in slot 222 or the bypass input opening 224. Once a specimen is detected, a technician or other operator may be prompted to enter, through a user input interface (not shown), identifying information for the specimen such as a specimen number, a lot number, a material and/or coating type, or a date and time. The user input interface may be a touchscreen panel, a keyboard, a bar code scanner or any other known means for entering data into a computer.

Once loaded, a specimen may be captured and transported to a labeling station 204, where the specimen is marked with an identifier such as a serial number or name associated with the identification information input by the operator. The labeling station 204 may include a pin stamp (not shown) that permanently marks the non-coated side of the specimen with the identifier. Of course, other known labeling means can be used and are within the scope of this invention including a laser or inkjet printer.

Figure 22:
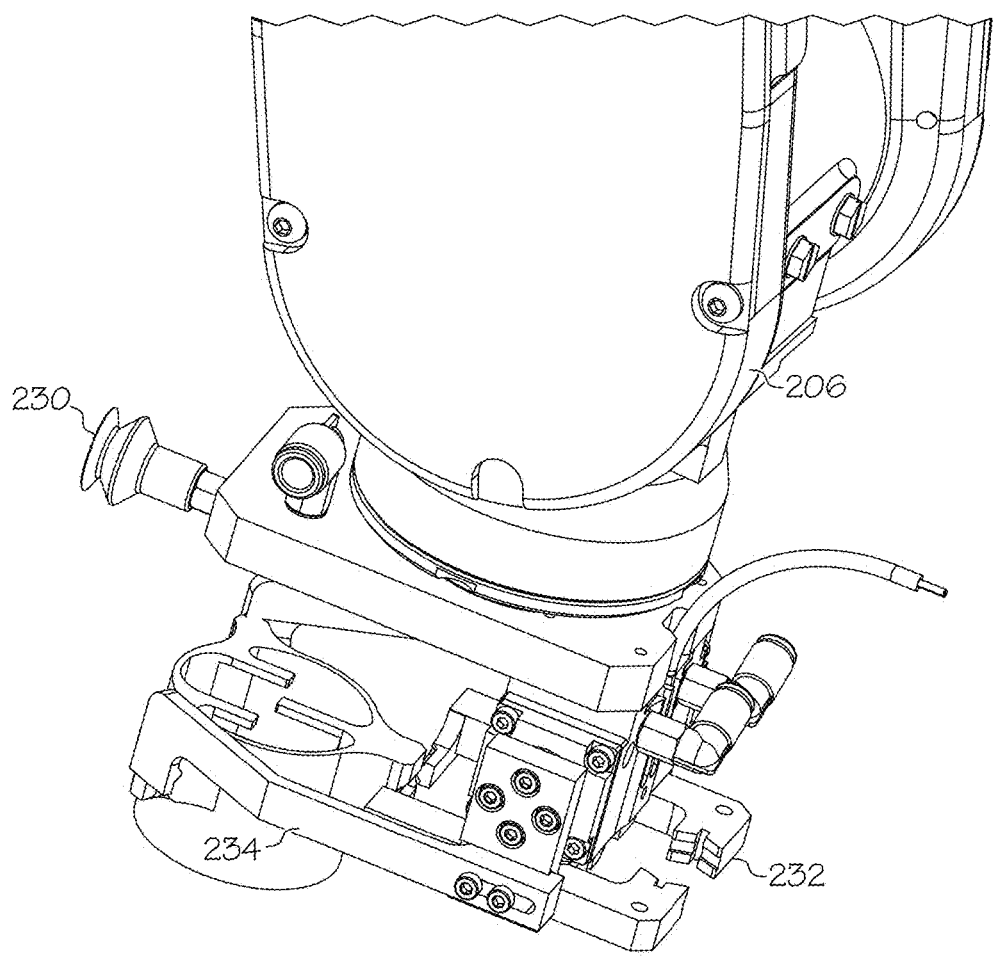
FIG. 22 is a perspective view of a robotic arm according to one embodiment.
Figure 23:
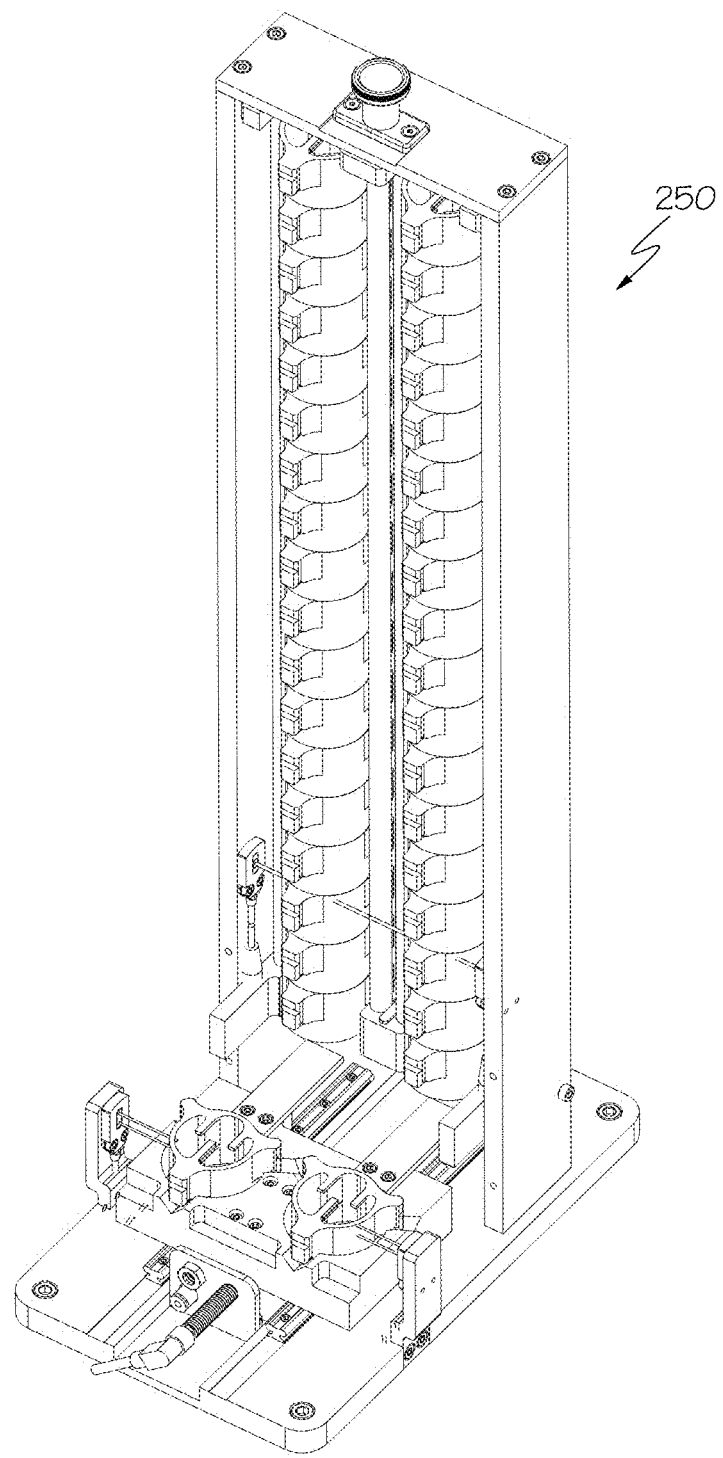
FIG. 23 is a perspective view of a specimen mounting cup rack.
Figure 24B:
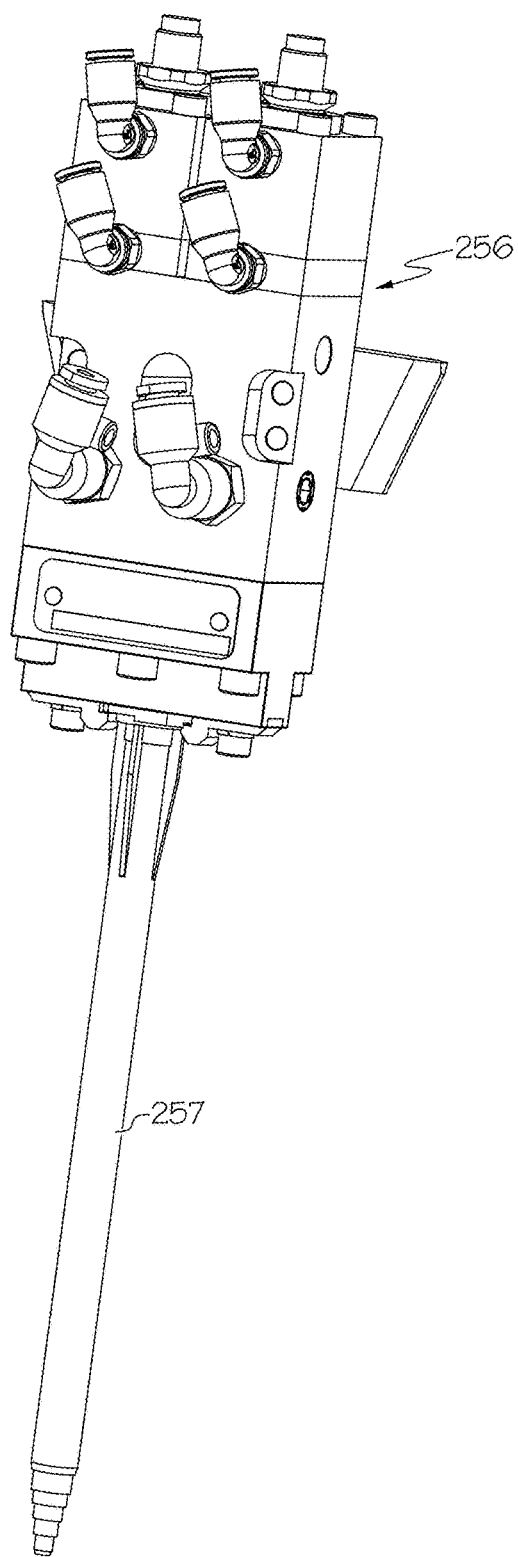
FIG. 24B is a perspective view of a resin dispenser.
Figure 25:
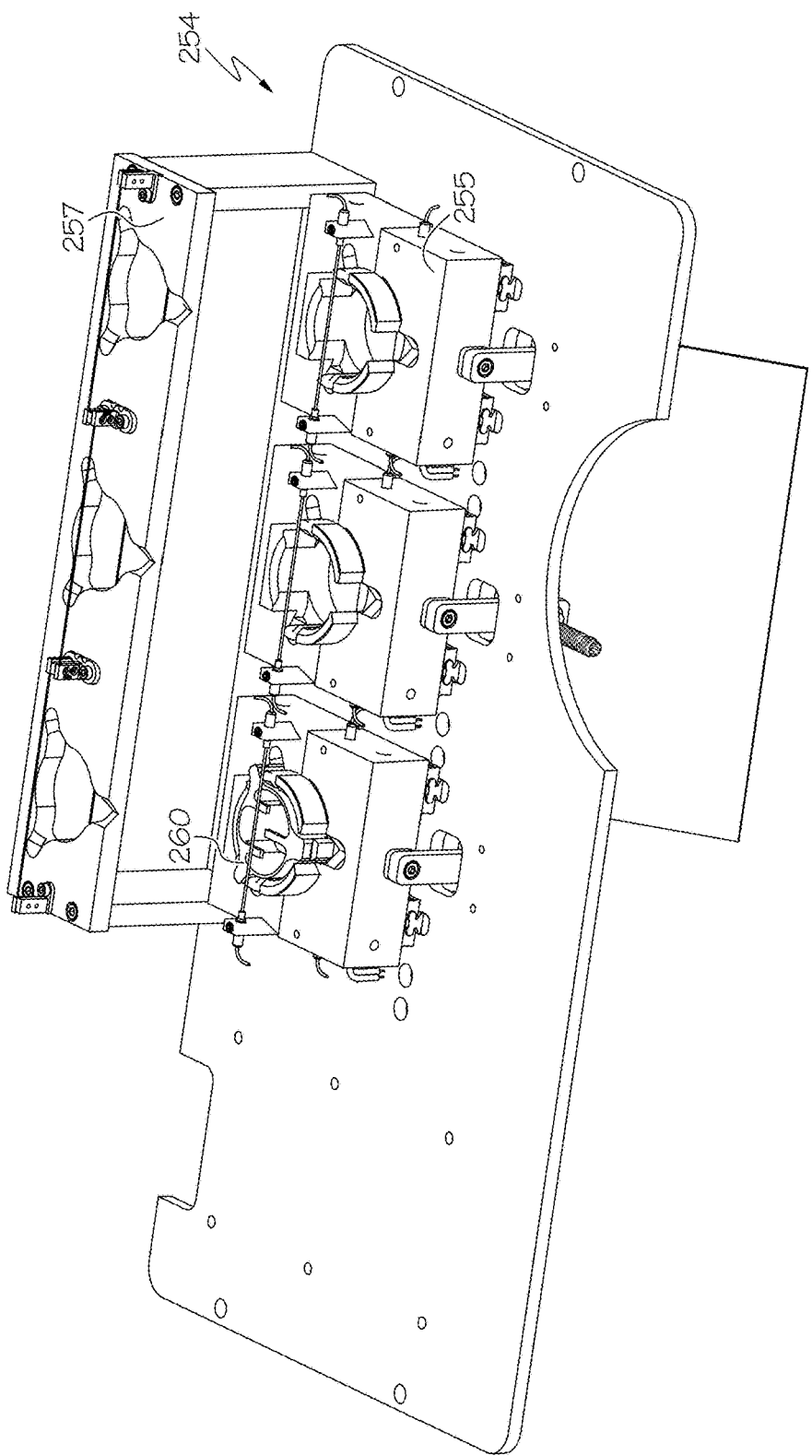
FIG. 25 is a perspective view of a heating station according to one embodiment.

An automated transport assembly, which may comprise a first robotic arm 206, is configured to move a specimen within the system. Specifically, the robotic arm 206 is configured to pick up and move a mounted or un-mounted specimen from or to the loading station 202, the labeling station 204, the preparation station 208, the mounting station 210, and the transport rail 212. Referring to FIG. 22, according to one embodiment, the arm 206 is equipped with multiple means for manipulating a specimen, whether mounted or un-mounted, including a suction cup 230, a coupon gripper 232, and a cup gripper 234. When a specimen is un-mounted and lying flat, the suction cup 230 may be used to pick up the specimen without having to grip the side edges of the specimen. Alternatively, the coupon gripper 232 is configured to grip the side edges of an un-mounted specimen. Once a specimen has been mounted in a specimen mounting cup, the cup gripper 234 is configured to grip the cup. In this manner, a single robotic arm can be used transport the specimen throughout the processes of loading, cutting and mounting, both before and after preparation of the specimen. In the alternative, or in addition to the robotic arm, the automated transport assembly may comprise a powered conveyor, such as belt, a rail guided system, a guided container system, or a hoist.

After a specimen is labelled, the robotic arm 206 may pick up the specimen and transport it to the preparation station 208, which includes a cutting device. According to one embodiment the preparation station includes a sectioning saw 52 and a rinsing station. Other methods for cutting the specimen include abrasive cutting, diamond wafer cutting, thin sectioning with a microtome, and laser cutting. Referring to the pictured embodiment, the robotic arm 206 may position the specimen on a cutting stage where it is cut by the sectioning saw 52 to produce a cut surface for analysis. If the specimen is a coated specimen, the coating, base material, and coating interface should be visible on the cut surface. Once the specimen is cut, the robotic arm 206 may pick up the specimen and transport it in front of a rinsing station where the specimen is sprayed with water or air to clean the cut surface before mounting. Using the coupon gripper 232 to firmly hold the specimen, the robotic arm 206 then moves the specimen to the mounting station 210.

With reference to FIGS. 21, 23-25, and 27-29, the mounting station 210 may include a rack 250 that is configured to hold and dispense a plurality of specimen mounting cups, a vacuum chamber 252, a heating station 254, a resin dispenser 256, and a resin reservoir 258. Each of these structures will be described in more detail below. Operation of the mounting station 210 is completely automated by a controller to provide consistent, hands-free mounting of specimens in a hardenable liquid for subsequent grinding and polishing. As used herein, the term controller is intended to broadly encompass any circuit (e.g., solid state, application specific integrated circuit (ASIC), an electronic circuit, a combinational logic circuit, a field programmable gate array (FPGA)), processor (e.g., shared, dedicated, or group—including hardware or software that executes code) or other component, or a combination of some or all of the above, that carries out the control functions of the machine or the control functions of any component thereof. The controller is operatively connected to the robotic arm 206 and the mounting station 210, and is operable to move the specimen through the mounting station according to a stored routine, without the need for human intervention.

The specimen mounting cups utilized in the mounting station are specially designed to serve two functions within the automated system. First, the specimen mounting cups are configured to hold a specimen in the cup in a desired orientation prior to embedding the specimen in resin. In particular, the cup is designed to hold the specimen in an upright position with the cross-section of interest (i.e., the cut surface of the specimen) resting on the bottom of the cup. Second, the cups include features that enable the automated system to grip the cup and angularly orient the cup to ensure that the mounted specimen is properly oriented for preparation and analysis. According to one embodiment the system utilizes specimen mounting cups 260 like the one shown in FIGS. 17-20.

Referring to FIGS. 17 and 20, the specimen mounting cup 260 is a generally cylindrical pot with an open top and a closed bottom 268. Extending into the interior of the cup are a plurality of fingers 262. These fingers may be flexible or substantially rigid so that when a specimen is inserted between the fingers they exert a gripping force to hold the specimen in place. In the embodiment shown in FIGS. 17-20, the fingers 262 extend inward from opposite interior sides of the cup but do not meet—leaving enough room for a standard metal coupon or other specimen to snuggly fit between the fingers in an upright position (see FIG. 27). With reference to FIG. 20, the cup may also include an upper group of fingers and a lower group of fingers to securely grip the specimen at two points, thus keeping the specimen upright and substantially perpendicular to the bottom face of the cup. The fingers may also be located so that the specimen can only be held in a single angular orientation within the cup. Of course, other means for holding the specimen in a desired orientation within the mounting cup are possible and are within the scope of this invention.

Referring now to FIG. 18, at least one indexing feature 264 protrudes from the exterior of the cup 260 so that the cup and the specimen within the cup can be properly oriented for preparation and/or analysis. In the pictured embodiment the cup includes three indexing features 264 that are equally spaced 120 degrees apart on the outside of the cup. One of the indexing features is different than the others (e.g., larger or differently shaped) so that the exact angular orientation of the cup can be determined within the system. In other embodiments, the indexing feature may be an indentation, rather than a protrusion, or any visible mark that can be used to identify the orientation of the cup within the system.

The specimen mounting cup 260 may also include gripping features to facilitate gripping and lifting of the cup by the first and/or second robotic arms 206, 216. In the pictured embodiment, the gripping features comprise notches 266 oriented perpendicular to the central axis of the cup and located around the perimeter of the cup. These notches 266 provide a surface where the cup gripper 234 can latch onto the cup securely.

Figure 27:
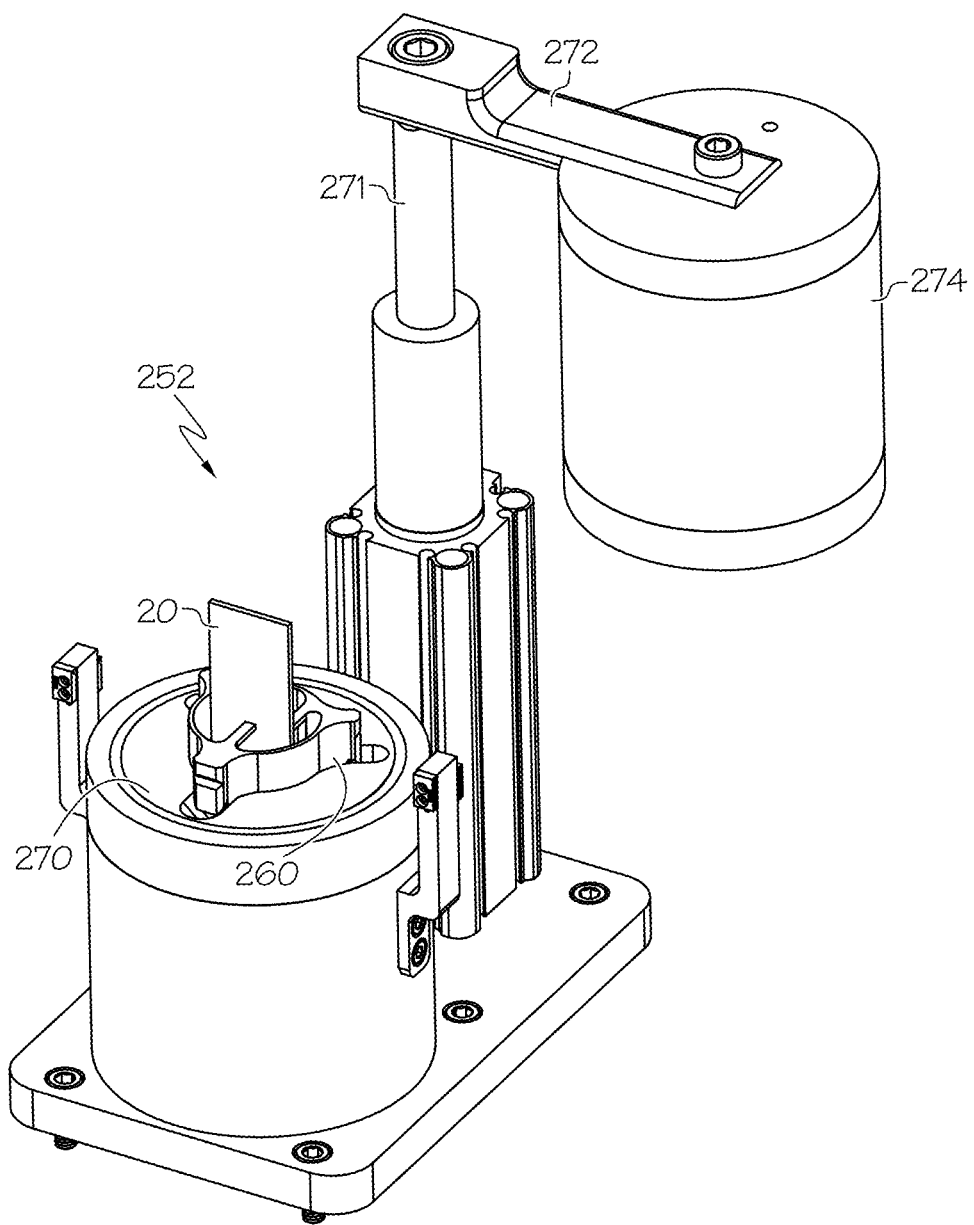
FIG. 27 is a perspective view of a vacuum chamber in an open position with a lid pivoted away to provide access to a specimen mounting cup holding a specimen.
Figure 28:
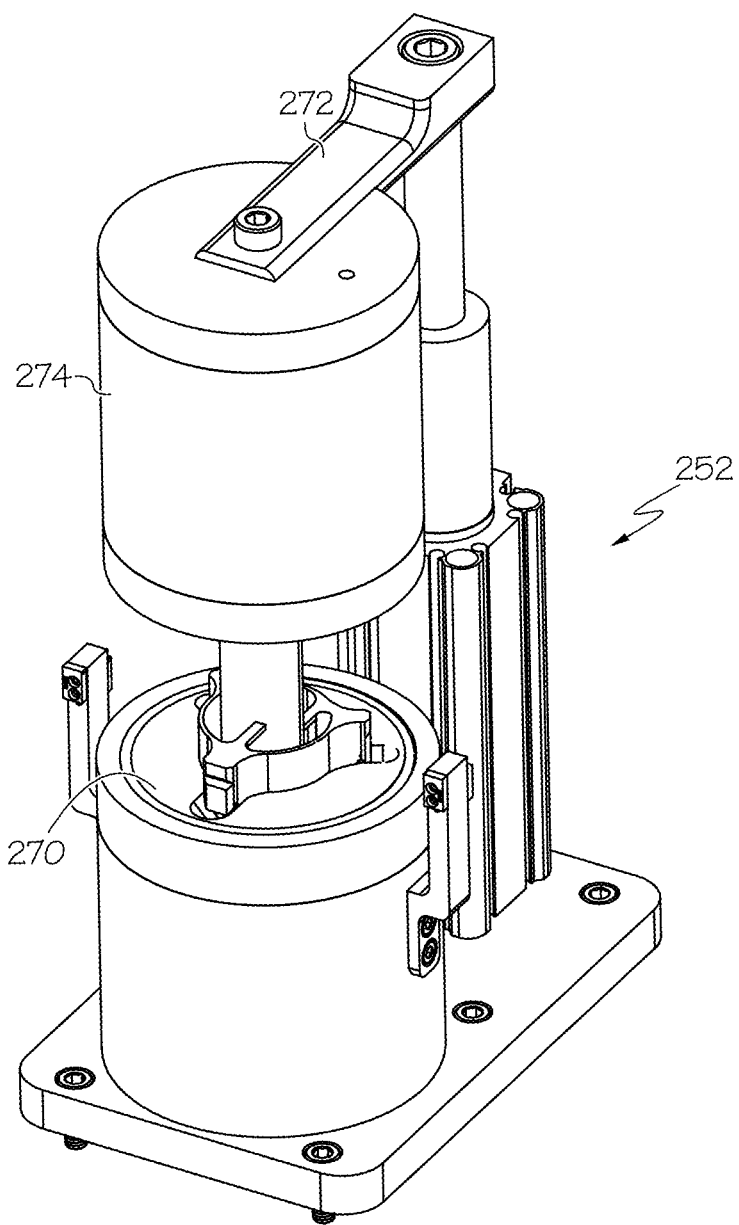
FIG. 28 is a perspective view of the vacuum chamber of FIG. 27 with the lid pivoted over a base.
Figure 29:
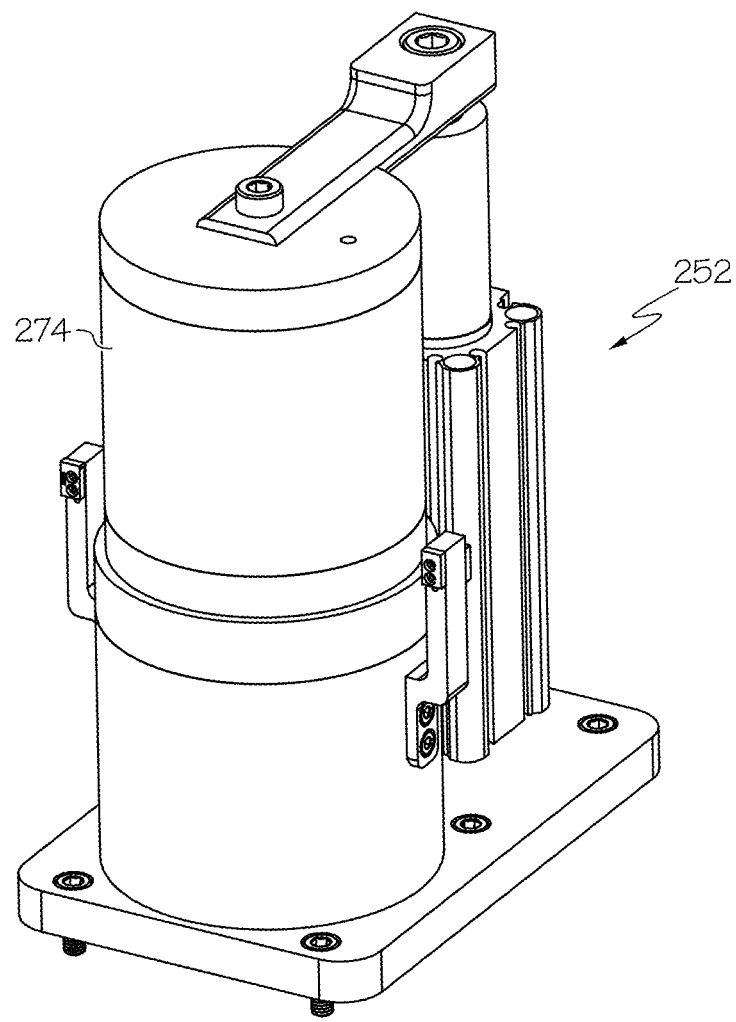
FIG. 29 is a perspective view of the vacuum chamber of FIG. 27 in a closed position.

According to one embodiment, mounting of a specimen at the mounting station 210 will generally proceed as follows. The robotic arm 206 will grip and transport an empty specimen mounting cup 260 from the rack 250 to a stage 270 of the vacuum chamber 252. With reference to FIG. 27, the stage 270 includes a recess configured to receive the specimen mounting cup 260. Specifically, the recess is configured such that the specimen mounting cup will only fit within the recess in one angular orientation. The vacuum chamber 252 further comprises an actuator 271, a pivotable arm 272, and a lid 274. The actuator 271 is configured to lift and pivot the arm 272 and lid 274 between an open position shown in FIG. 27 and a closed position shown in FIG. 29.

After an empty specimen mounting cup 260 is positioned on the stage 270 of the vacuum chamber 252, the robotic arm 206 then grips and transports a cross-sectioned specimen from the preparation station 208 to the vacuum chamber 252. Specifically, the robotic arm 206 is operable to rotate the specimen and insert it into the specimen mounting cup in a predetermined, desired orientation (as shown in FIG. 27) with the cut face of the specimen facing downward and adjacent to the bottom of the cup.

A resin dispenser 256 connected to a resin reservoir 258 by tubing (not shown) is moved to the vacuum chamber 252 to dispense a liquid, hardenable resin into the specimen mounting cup 260. The resin may be a two-part epoxy including, for example, Beuhler EpoThin 2 Epoxy, which secures the specimen within the cup. The resin dispenser 256 may be configured for use with a supply of disposable mixing nozzles 257 to prevent clogging of the dispenser. After use, the nozzle 257 is removed from the dispenser and dropped down a waste chute into a waste container. According to one embodiment, the resin dispenser 256 is picked up and moved from a docking station to a position above the vacuum chamber using the robotic arm 206. Of course, the dispenser could be moved by other means. Once the resin is dispensed into the specimen mounting cup 260, the vacuum chamber is closed and a vacuum is applied to impregnate the resin into the specimen.

A heating station 254 includes a heating tray 255 configured to hold a plurality of specimen mounting cups 260 containing resin. By applying heat through the heating tray 255, the resin can be cured (i.e., hardened) more quickly to expedite the mounting process. In addition, to the heating tray 255, a cooling tray 257 may also be provided that is configured to hold a plurality of specimen mounting cups.

Figure 26:
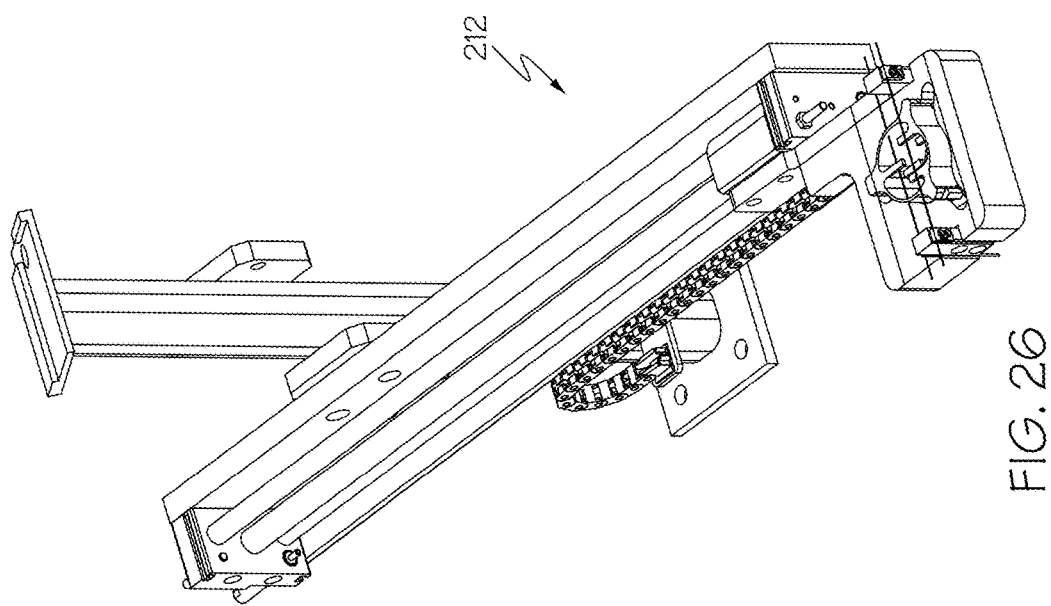
FIG. 26 is a perspective view of a transportation rail assembly according to one embodiment.

Once the resin is fully hardened, the specimen mounting cup with the specimen inside, which may sometimes be referred to as a sample, will be transported to a material removal station, which may be a grinding and polishing station 214. According to other embodiments, the material removal station may include milling tools and/or systems for performing laser ablation, focused ion beam ablation, or sonic ablation. In on embodiment, the sample is transported using a sample transportation rail 212 shown in FIG. 26. In particular, the first robotic arm 206 may move the sample from the heating station to transportation rail 212. The transportation rail then transports the sample from the mounting station 210 to the grinding and polishing station 214 where the second arm 216 grips and moves the sample to a platen. Grinding and polishing proceed as described above. However, according to the presently described embodiment, the thin bottom wall 268 of the specimen mounting cup 260 is abraded away in the first grinding step to reveal the cut surface of the specimen for polishing.

Figure 10:
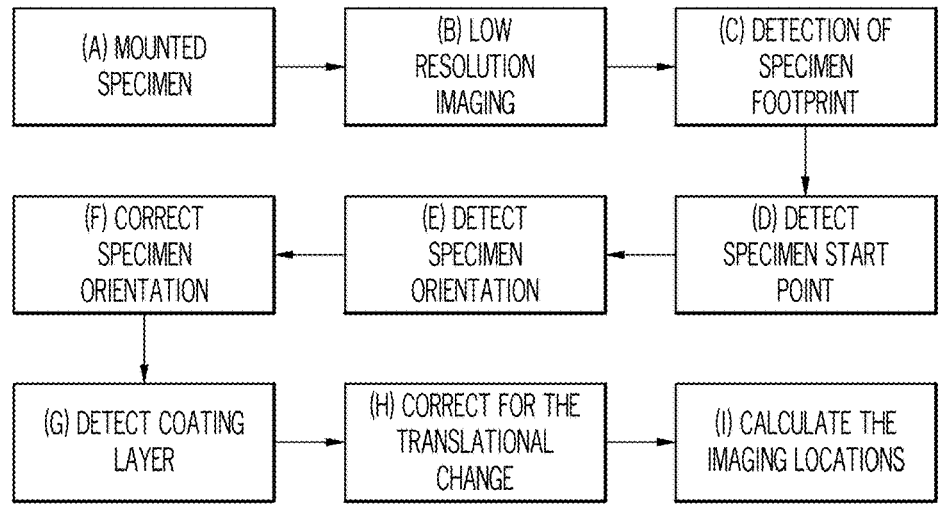
FIG. 10 depicts a flow control diagram of a metallographic coupon positioning system for coating quality inspection in an automated metallography coupon coating analysis configuration according to one or more embodiments shown and described herein.

In one embodiment the microscope is a Zeiss digital microscope, which can take sharp images at several magnifications. This microscope is equipped with a high resolution camera for digital documentation and can capture both color and grayscale images. The microscope focuses automatically on the prepared sample using the autofocus feature. The mosaic function and motorized stage allow the capture of large surface specimens automatically. The microscope acquires images at user defined coordinates with utmost precision consistently. The automated microscope may be used to view and/or image the cross-sectional cut and provide a data set for analysis of the coating as described in FIG. 10. To examine the specimen, it must be placed on the microscope stage and oriented so that the point on the specimen to be evaluated (e.g., the coating-substrate interface) can be located. FIG. 10 (*a*) is the input to the positioning system which is a mounted specimen placed on the microscope stage by the robotic arm. In one embodiment, the microscope may automatically change the objective lens to 1× magnification and acquire a mosaic of images that cover the entire mount region inclusive of the specimen as indicated at FIG. 10 (*b*). An algorithm is built that enables the user to scan the mosaic image and detect the actual specimen region within the mosaic based on the image pixel intensities as depicted in FIG. 10 (*c*). A starting point to detect the coating region is determined, typically the left corner of the specimen and automatically adjusted to focus on the interface between specimen and the mount (FIG. 10 (*d*)). The specimen is then fitted with a desired shape such as rectangle or ellipse to calculate/determine its orientation (FIG. 10 (*e*)). The orientation of the specimen is the angle it makes with long (X) axis of the microscope stage. Several low resolution images are taken to calculate the orientation angle of the specimen which angles is fed back to the specimen-handling robot. The robot arm picks up the specimen from the microscope stage, rotates it by an appropriate angle and places it back on the stage. This enables the long axis of the specimen to coincide with long axis of the stage. This constitutes rotation corrected specimen placement (FIG. 10 (*f*)). The top of the coating layer is then detected by identifying the interface between the mount material and coating material based on the difference in their texture. Similarly, the approximate interface between coating and its base metal is also detected (FIG. 10 (*g*)). Because the actual coating region is sandwiched between the mount and the base metal, the translational changes are calculated for the high resolution image to be taken at the approximate center of the coating region (FIG. 10(*h*)). Actual imaging locations are calculated based on the coating thickness as well as the specimen dimensions. The pixel dimensions are recalculated for different objective lenses and the imaging location is calculated using the coating mid-point and the field of view dimensions at a required resolution (FIG. 10 (*i*)). The automated microscope may be an optical microscope such as a Zeiss digital microscope, a scanning electron microscope or the like.

The microscope may be equipped with a high resolution camera for digital documentation and can capture both color and grayscale images. The microscope focuses automatically on the prepared sample using the autofocus feature. A mosaic function and motorized stage allow the capture of a large portion of the cut surface of the specimen 20 automatically. The microscope acquires images at user defined coordinates consistently. The microscope may also be an x-ray camera to do real-time point-by-point mapping of the crystallographic orientation of the cross-sectional cut 45 of the specimen 20. The microscope and/or the x-ray camera may be used to evaluate one or more sets of properties of the specimen 20. A display may be used to present a pass/fail result and/or the image from the automated microscope and/or the x-ray camera.

A microprocessor unit may be used to control the automated microscope and/or x-ray camera. The microprocessor may have a computer-readable medium and a processor. The computer-readable medium (i.e. memory) may have a stored algorithm that is used by the processor to algorithmically evaluate the image of the cross-sectional cut 45 and transmit the result of a pass or a fail evaluation of the coating. In some embodiments the processor may algorithmically evaluate one or more sets of properties of the specimen to transmit the result of a pass or a fail evaluation of the coating.

Figure 11:
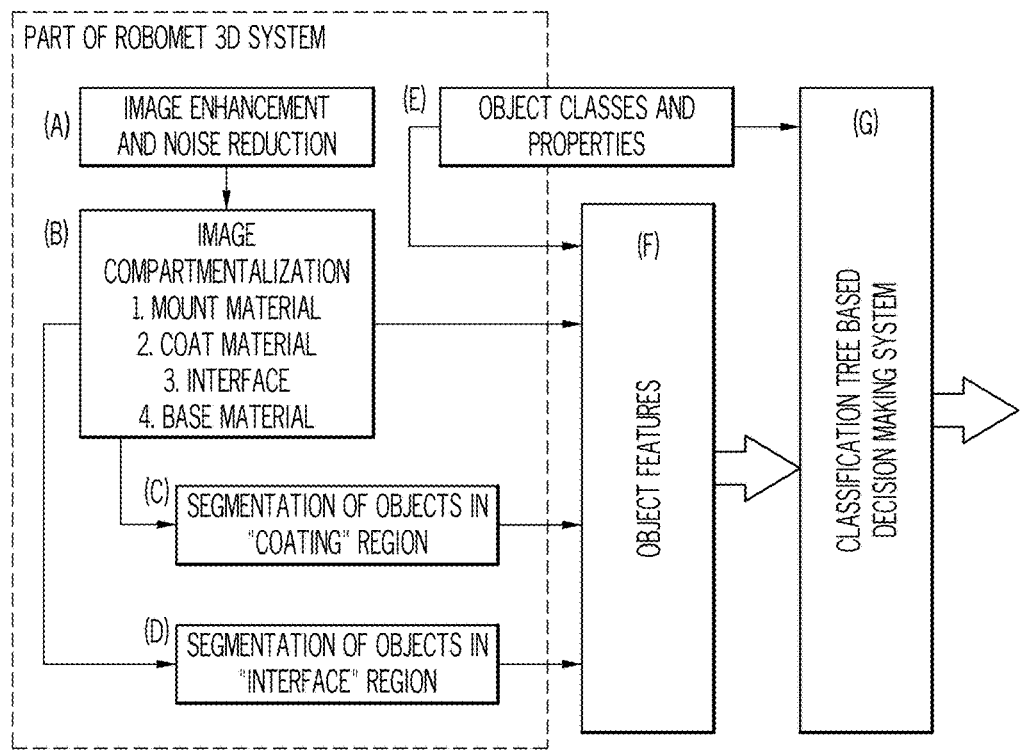
FIG. 11 depicts the flow control diagram for an analytics system to identify different components in the coated coupon in an automated metallography coupon coating analysis configuration according to one or more embodiments shown and described herein.
Figure 16:
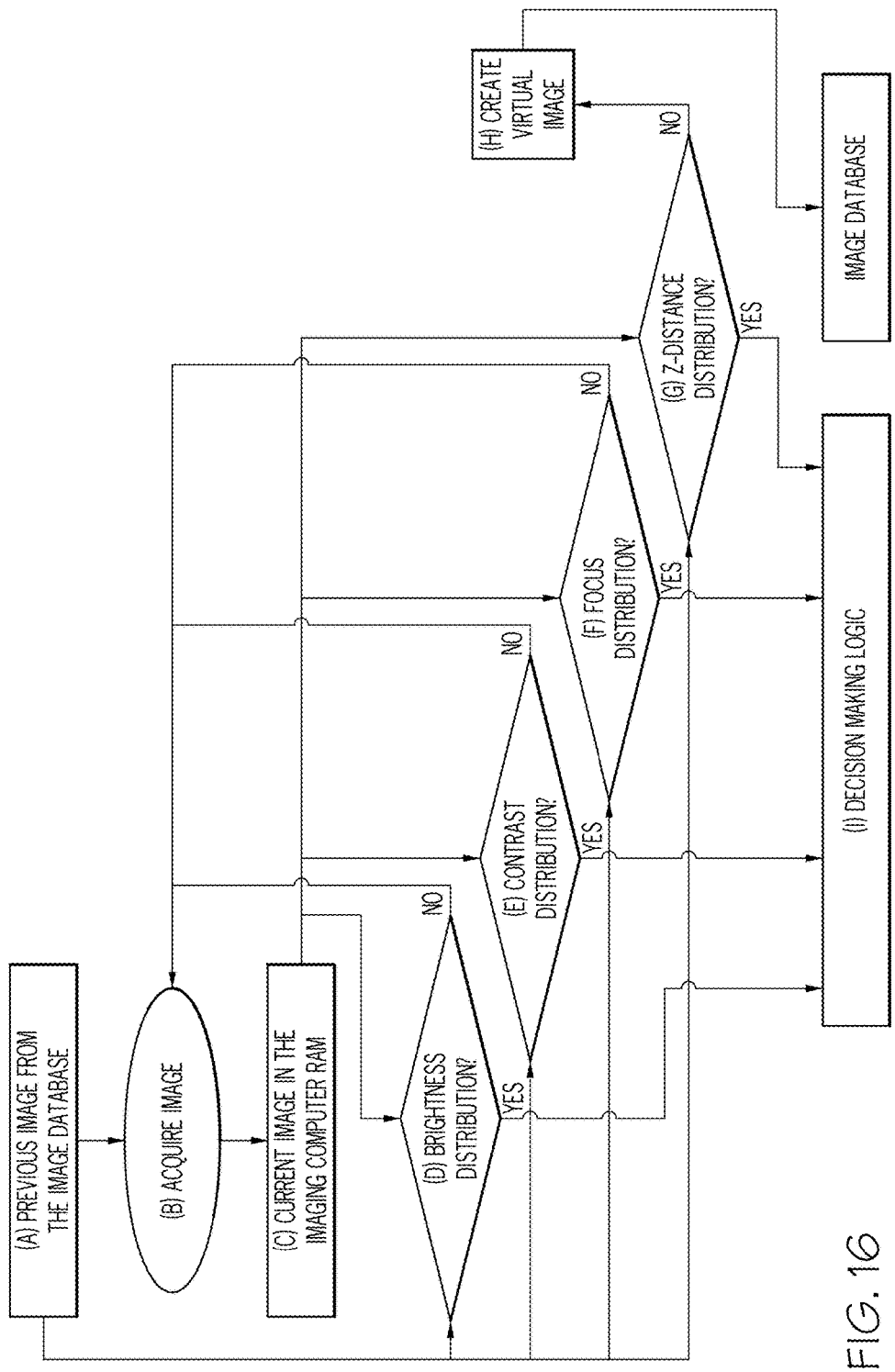

After high resolution images are collected from appropriate regions, several image analysis and pattern recognition algorithms may be used to provide a level of machine intelligence for supporting the feature quantification and decision making. One step in this direction is the enhancement of the image features and reduction of the noise (FIG. 11 (*a*)). FIG. 12 (*a*) shows an original representative image of coating material. As explained in more detail in reference to FIG. 16, a sequential and a feedback system from a number of filters (see FIG. 16, (*d*)-(*g*)) including, but not limited to, anisotropic diffusion filter, reaction-diffusion filters, coherence enhancement, structural smoothing, etc. may be applied on a wavelet transform based pyramidal representation of the image data. This enhances the characteristics of individual features such as pores, oxides, voids, unmelted particles, carbides, contamination etc., in the images. In one embodiment, the second step is to segment the different regions in the image into a region of mounted material, a region of coating material, interface between coating and base-metal and the base-metal region. This is accomplished by classifying the pixel based on pixel context features, amount of high frequency information present, and the pixel intensity changes at various scale space transformed data points (FIG. 11 (*b*), FIG. 12 (*b*)). Every object in the coating region is then segmented by a combination of edge detection and region growing segmentation techniques. See References 4 and 5 below which are incorporated herein in their entirety by reference. This object level segmentation is done in scale space pyramid, and object continuity in a scale space is then analyzed to differentiate between oxides, carbides, cracks and voids (FIG. 11 (*c*), FIG. 12 (*c*)). The interface between base-metal and the coating is detected by base-metal and coating region characterization. All the objects in the coating region that are located within a certain distance such as 5 pixels in base metal to 5 pixels in coating material at 200× magnification from the interface are considered as interface region objects (FIG. 11 (*d*), FIG. 12 (*d*)). Several statistical, textural, amplitude, geometric and multi-frequency features (FIG. 11 (*f*)) are calculated for each object in every image scale that is processed. Based on training data sets and the ASTM standards, a detection/classification/quantification tree structure (FIG. 11 (*g*)) is established to identify objects and build reports to facilitate evaluative ranking of the coating process. The one or more set of properties of the specimen 20 may correspond to the characteristics of the coating. The characteristics may include the thickness of the coating, uniformity, color, foreign contaminants, etc.

Figure 13:
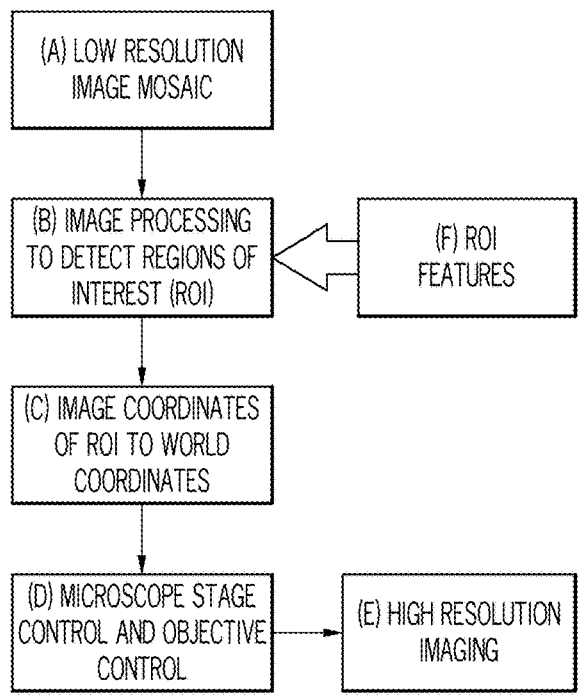
FIG. 13 depicts a flow chart whereby a region of interest (ROI) such as a coating interface is identified and used to provide stage and objective control for high resolution imaging.

As shown in FIG. 13, block (*a*), image of the whole specimen is collected as a low resolution mosaic of image tiles. The low resolution image is subjected to image analytics and the possible regions of interest are automatically selected. Region of interest (ROI) features can be predefined as boundary of the objects, high frequency region, particular type of texture or brightness etc. See Reference 8 below which is incorporated herein by reference. It is also possible manually to indicate the regions of interest on a low resolution image. The computer can be programmed to build a feature characteristics table of the region of interest and capture high resolution good quality images whenever it encounters such regions in the specimen. In block (a) "Low resolution image Mosaic," the system collects low resolution images of consecutive areas in the large area specimen with a fixed overlap. Then each image is assembled with a predetermined overlap and automatically searches for a best match in the image features such as boundary, gradient magnitude or texture of statistical equivalency by moving one image relative to the other in X and Y directions within a predefined range. Best similarity measure point (calculated as a correlation coefficient, Euclidean distance or any other similarity measure based on pixel statistics) will be selected and the two images are stitched with that overlap. Similarly the remainder of the images are also stitched together to form a large mosaic showing either entire specimen or a large area of the specimen. At this point the user can either mark the regions of interest using a mouse driven software or simply let the software decide the regions of interest such as object boundary regions (Sobel detector, canny Detector, etc.), blobs (binary segmentation, watershed, region-growing, model based segmentation, template matching, etc.), textured regions (Haralick's statistical textures, Gabor filters, Malik filters, Laws Texture filters, etc.), high-frequency regions (FFT filters) etc., based on respective region identification filters. These filters use a predetermined feature range to identify the importance of the region. Blocks (b) "Image Processing to Determine the ROI" and "ROI features" (f) together accomplish this task. A linear transformation of the coordinates of the regions of interest to world coordinates that defines those regions on the actual specimen is accomplished by geometric transformations in block (c) "Image Coordinates of ROI to World coordinates". The imaging software then understands the list of new positions it has to move to and what resolution images of the ROI have to be captured (block (d) "Microscope stage control and objective lens control"). The high resolution images thus captured (e) are once again stitched together by mosaicking software and sent to further analysis by experts.

The same principle illustrated in FIG. 13 can be extended to identify faults in the specimen or errors in specimen preparation that causes a scratch or dent on the specimen surface, dirt or water or other foreign objects on the specimen that result in bad quality image; and relay the information back to polishing cleaning station with required parameters to rework the specimen. With this mechanism the quality of the acquired images can be controlled to be consistent throughout the 3D image stack.

Figure 14:
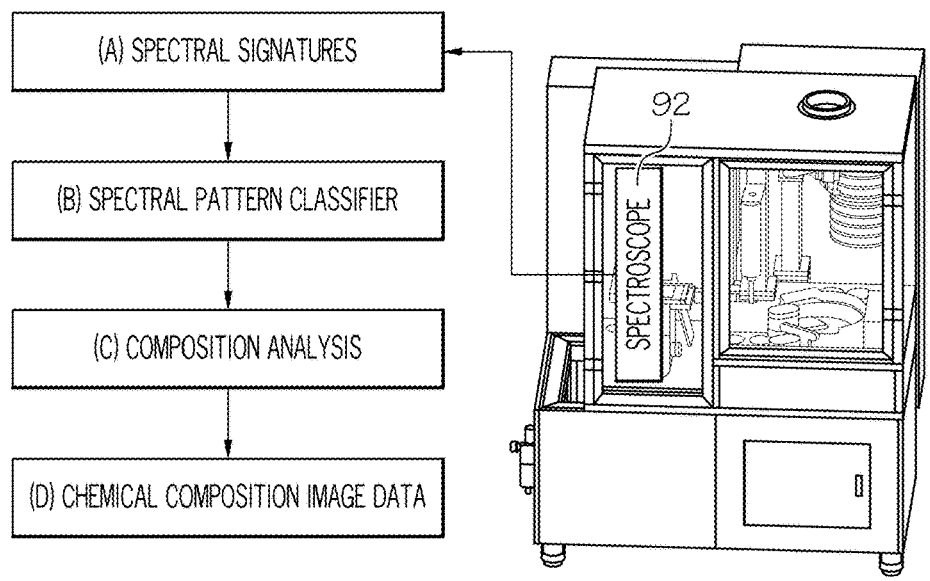
FIG. 14 depicts a flow control diagram for acquiring chemical composition maps by spectral scattering (e.g. Raman scattering and/or other spectrographic scattering techniques) and to construct chemical composition micrographs showing the chemical composition and structure for a large continuous volumetric regions of interest in a 2D/3D space defined by the specimen for 2D/3D automated metallography microstructure composition analysis configuration, according to one or more embodiments shown and described herein.

FIG. 14 illustrates the embodiment in which the system includes a spectroscope 92 to analyze the specimen. Spectroscopy is the study of interaction of the electromagnetic waves with the materials. Raman spectroscopy, infrared spectroscopy, X-ray spectroscopy, photoelectron spectroscopy, Raman measurements can be used for structural characterization for semiconductors and super conductors. It has been used to describe the shape, size and position of first order phonon bands in semiconductors. The Raman spectrum and map can also provide information about stress, crystal lattice disorder, phase separation of supersaturated solution and homogeneity. Raman spectroscopy is very often used to characterize the structure, environment and dynamics of polymeric materials. The chemical composition of the structure of polymers has been studied during online processing and development in factories. The technique has been used in forensics to identify traces of plastic explosives through molecular level detection. One very significant benefits of Raman spectroscopy is the analysis of aqueous samples, as a result it can be used to detect hazardous materials in trace amounts in water. Infrared spectroscopy can be used to identify new amorphous materials, nano composites, rocks and minerals, polymer materials etc. Surface chemical analysis can be easily conducted by EDS/WDS technologies that are integrated with scanning electron microscope.

In general, the output of the spectroscopy is a noisy pattern of peaks over a range of wavelengths. The intensity of the peaks, the location of the peaks, and the predefined neighborhood pattern of the peaks facilitate identification of the chemical composition of a material at a point from where the spectral signature is emitted. In addition to Raman, other forms of spectroscopy technologies such as NMR spectroscopy amd infrared spectroscopy can be used by either placing the probes directly in the imaging chamber or building individual spectral signature collection chambers to where the specimen is moved and the information is acquired. Both fiduciary marking and/or use of optical images may be used to pin point the regions from where spectral signatures (a) would be collected. Scale-space theory and wavelet transform based filters allow one to visualize both spatial location (time or wavenumber coordinate) and the frequency content of the signature. Scale-space theory based filters can be used to reduce noise and enhance peaks. These filters enable the noise reduction based on the intensity of the peaks but also based on the context in which the peaks are located. Possible patterns can be extracted at step (b) from the chemical composition signature and ranked based on their repeated presence within the spatial vicinity of the specimen point from where the signatures are collected. With the help of the lookup tables that provide wavenumbers for different chemicals, chemical composition maps of the material surface can be developed at step (d). By repeating the process at different depths and providing spatial continuity context, then volumetric chemical composition of the material can be built up.

Figure 15:
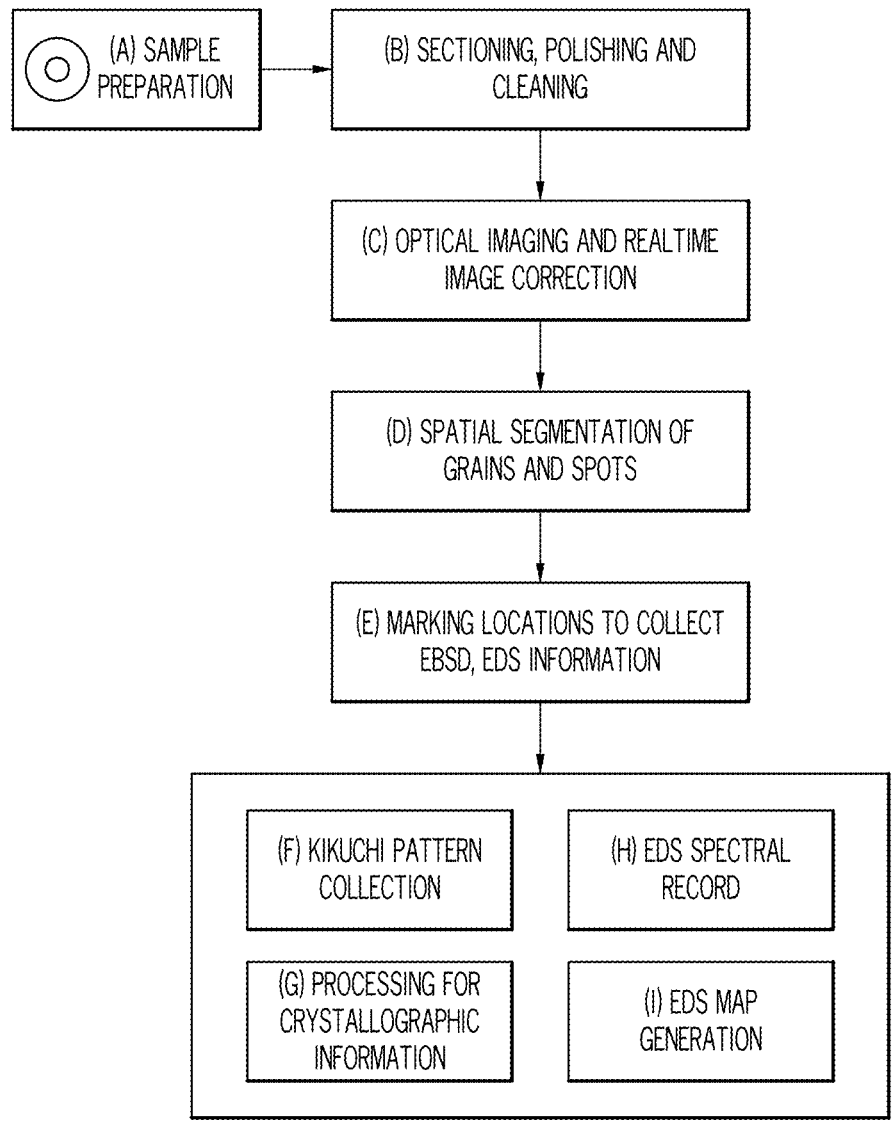
FIGS. 15 and 16 depict flow control diagrams for acquiring EBSD and EDS maps from a large volumetric region by hybrid opto-electronic imaging and constructs electron micrographs showing the orientation of the crystal structure for large continuous volumetric regions of interest in a 2D/3D space defined by the specimen for 2D/3D automated metallography microstructure analysis configuration, according to one or more embodiments shown and described herein.

It is well known that a material's internal structure can control its properties. Thus, characterization of internal structure/property relationships is a key to understanding, predicting, and tailoring the properties toward specifically engineered uses of materials. In addition to historical advancements, recent automation of characterization has led to acquisition and storage of massive quantities of data, beyond the scope of direct human interpretation. A multi-modal image acquisition instrument and an efficient algorithmic approach that focuses on the micro structural aspects of an engineering alloy system can be used. Optical microscopy, EDS and EBSD can be integrated in real time with auto-correcting capabilities to ensure high quality data output. In two dimensions (2D), it is feasible to manually segment and combine the data together to achieve a multi-scale and multi-modal representation. EBSD/EDS capable scanning electron microscope and a set of real-time image analytics to guide multi-modal imaging to reduce the collection of redundant information can be incorporated into the system. Data fusion technologies can then be used to fill the spatially sparse multi-modal data matrix. As shown in FIG. 15, "Sample preparation" block (a) prepares the sample by cutting, mounting and placing in a sample holder. The sample will be transferred to automated polishing and etching stations as represented by "sectioning, polishing and cleaning" block (b). This is currently a part of the Robomet.3D technology available from UES, Inc. The polished and cleaned specimen is moved to the optical imaging station and optical images of relevant regions of interest are collected. The image quality is controlled by "real time image correction" block (c) that compares the statistical features and amplitude features of the current image with the previous image and determines whether additional polishing and/or cleaning is required and also adjust light and focus values. The analytics software (e.g., R3Danalytics) filters then segment the grains and precipitate structures in the optical image as shown in block (d). When required these structures are compared to previous image in the same 3D block to identify new grains and new precipitates. The coordinates of the new grains and new precipitate points are then transferred to electron imaging (block (e) "Marking locations to collect EBSD and EDS information"). EBSD and EDS information at all the points of interest (newly found grains and precipitates) are collected. The section with blocks (f) "Kikuchi pattern collection" and (g) "processing for crystallographic information" work together to generate EBSD maps which provide the information about grain crystallographic orientation. A tandard Kikuchi pattern analysis algorithm is used to accomplish this. Blocks (h1) "EDS spectral record" and (i) "EDS map generation" together provide chemical composition analysis of the surface of the sample being imaged. Due to the mechanical movements and chemical polishing processes required to prepare the material for imaging, it is hard to obtain uniform axial resolution, exact grain registration, and at times, matching image statistics for all optical sections in the data stack. Also, due to difficulty in obtaining the flat surface by etching and polishing, specifically in alloys and compound materials, it is possible that all the regions in the image are not in focus. An image analytics tool (FIG. 16) set acts in a sequence to identify artifacts and errors in the acquired image (h) and attempts to correct it either digitally or by reacquiring the image data. This analytics system includes of four distinct image feature measurement blocks (d) "Brightness distribution", (e) "Contrast Distribution", (f) "Focus Distribution", (g) "Z-distance distribution" and a system to compare the feature distributions to either preset standards or with that of previously collected data (a) "decision making Logic" block (i). Localized image histogram, background brightness variation patterns in the form of low frequency image, local contrast pattern and local binary patterns (See Reference 9 below which is incorporated herein in its entirety by reference) together forms the Brightness distribution. Local contrast patterns, gradient magnitude and phase patterns, pixel grouping (as defined by mean-shift filtering) patterns together define contrast distribution in the image. See Reference 10 below which is incorporated herein in its entirety. In general, high-end microscopes provide images that are in focus all through the field of view. Regions that are out of focus can be identified by analyzing localized power-spectrum patterns. If there is a significant out of focus regions, these might be caused by the presence of water drop artifacts or the specimen surface not being flat. In such cases the specimen is sent back for further fine polishing cleaning and drying to acquire better quality image (b). The focus distance of every image also measures how much material is polished off at every sectioning process. If not enough material is removed the specimen can be sent back to the polishing station for further removal of material. If too much material is removed, the process has the capability to create an additional intermediate image (h) by appropriate interpolation process to maintain consistent image thickness. In summary, this software is capable of automatically analyzing images (c) in the 3D data, correcting for common image properties such as brightness, contrast, etc. to be consistent throughout the stack. The software is also capable of segmentation (through a bank of segmentation filters) of the grains, and precipitates. The segmented grains and precipitates are uniquely labeled and checked for their continuity from the previous image (a) in the 3D data stack. If they are newly formed grains, the locations are noted, converted to world coordinates and passed on to electron imaging station for addition information collection.

Algorithms disclosed herein may be embodied in hardware and/or in software (including firmware, resident software, micro-code, etc.). The system controller may have at least one processor and the computer-readable medium. A computer-usable or the computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of the present disclosure may be written in a high-level programming language, such as C or C++ or C#, for development convenience. In one embodiment, Ladder Logic is the software used to control the system. It was chosen because it increases machine efficiency, is easy to expand and is understood by most technicians. The software represents programs graphically, making it particularly appealing for step-wise processes. Control of the AIM system will occur via a Programmable Logic Controller (PLC). In addition, computer program code for carrying out operations of the present disclosure may also be written in other programming languages, such as, but not limited to, interpreted languages. Some modules or routines may be written in assembly language or even micro-code to enhance performance and/or memory usage. However, software embodiments of the present disclosure do not depend on implementation with a particular programming language. It will be further appreciated that the functionality of any or all of the program modules may also be implemented using discrete hardware components, one or more application specific integrated circuits (ASICs), or a programmed digital signal processor or microcontroller.

REFERENCES

1) ASM (American Society for Metals) hand book Volume 9
2) J. C. Russ, Image Processing handbook, CRC Press, 1996.

3) G. Aubert and P. Kornprobst, Mathematical Problems in Image Processing, Partial Differential Equations and the Calculus of variations, Springer Verlag, New York, 2000.
4) Umesh Adiga, "An integrated approach for segmentation of 3-D confocal images of a tissue specimen", J. Microscopy Research and Techniques, Vol. 54, pp. 260-270, 2001.
5) Umesh Adiga and B. B. Chaudhuri, "An efficient method based on watershed and rule based merging for segmentation of 3-D histo-pathological images", J. Pattern Recognition, Vol. 34/7, pp-1449-1458, 2001.
6) Laptev I; Lindberg T; Tracking of multi-state hand models using particle filtering and a hierarchy of multi-scale features, In: M. Kerkhove Eds. *Scale-space and morphology in computer vision*, 2001, LNCS 2106, pp. 63-74.
7) Rizon M; Yazid H; Saad P; Shakaff A Y; Saad A R; Mamat M R; Yaacob S; Desa H and Karthigayan M; Object Detection using Geometric Invariant Moment, *American Journal of Applied Sciences*, 2006, 2, pp. 1876-1878.
8) Haralick R. M; Statistical and structural approaches to texture, *Proc. IEEE*, 1979, 67, pp. 786-804.
9) Pietikäinen M; Image Analysis with Local Binary Patterns, *Image Analysis: Lecture Notes in Computer Science*, 2005, 3540, pp. 115-118.
10) Bashar M K; and Ohnishi N; Image Retrieval by Local Contrast Patterns and Color, G. Bebis et al. (Eds.): ISVC 2006, LNCS 4292, Springer-Verlag Berlin Heidelberg, pp. 136-145.
11) Kruskal, J B; Multidimensional scaling by optimizing goodness of fit to a nonmetric hypothesis. *Psychometrika*, 1964, 29, pp. 1-27.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed:

1. An automated metallographic system for cutting, mounting and analyzing a specimen, the system comprising an outer housing, a loading station, an automated transport assembly, a preparation station, a mounting station, a material removal station, an analyzer, a user input interface, and a controller;
    wherein the preparation station and the mounting station are housed within the outer housing;
    wherein the loading station comprises an input opening through the outer housing configured to receive an un-mounted specimen;
    wherein the preparation station comprises a cutting device configured to cut the un-mounted specimen to provide a cut surface for analysis;
    wherein the automated transport assembly is configured to transport the un-mounted specimen from the preparation station to the mounting station;
    wherein the mounting station comprises a resin reservoir and a resin dispenser, the mounting station configured to mount the specimen in resin with the cut surface of the specimen in a predetermined orientation;
    wherein the material removal station is configured to remove material from the cut surface of the mounted specimen;
    wherein the analyzer is configured to obtain an image of a surface of the mounted specimen;
    wherein the user input interface is configured to receive identification information associated with the un-mounted specimen; and
    wherein the controller is programmed to operate the cutting device, the automated transport assembly, and the resin dispenser.

2. The system of claim 1 further comprising a labelling station configured to label the un-mounted specimen with an identifier associated with the identification information received through the user input interface.

3. The system of claim 1, wherein the automated transport assembly comprises a robotic arm.

4. The system of claim 3, wherein the robotic arm includes a first gripper configured to grip the un-mounted specimen prior to mounting the specimen in resin and a second gripper configured to grip the mounted specimen mounted in resin.

5. The system of claim 4, wherein the robotic arm further includes a suction cup configured to releasably attach to the un-mounted specimen for lifting the specimen.

6. The system of claim 1, wherein the loading station further comprises a bypass input opening through the outer housing configured to receive a pre-mounted sample comprising a specimen mounting cup that has been pre-loaded with a specimen.

7. The system of claim 6, wherein, when the specimen mounting cup is received through the bypass input opening, the automated transport assembly is configured to transport the specimen mounting cup from the bypass input opening to the mounting station, bypassing the preparation station.

8. The system of claim 1, wherein the mounting station further comprises a rack configured to hold a plurality of specimen mounting cups, each specimen mounting cup configured to receive and hold a respective specimen with a cut surface of the specimen facing downward adjacent to the bottom of the cup.

9. The system of claim 8, wherein each specimen mounting cup includes a plurality of integral fingers extending into the interior of the cup, the fingers configured to engage opposite sides of the specimen inserted into the cup and to hold the specimen in the predetermined orientation.

10. The system of claim 1, wherein the mounting station further comprises a vacuum chamber configured to receive a specimen mounting cup loaded with the specimen and resin and to apply a vacuum to the specimen mounting cup.

11. The system of claim 1, wherein the mounting station further comprises a heating station including a heating tray configured to hold and heat a plurality of specimen mounting cups containing resin.

12. The system of claim 1, wherein the material removal station comprises a plurality of platens configured to grind and polish a cut surface of a specimen.

13. The system of claim 1, wherein the loading station further comprises a bypass input opening through the outer housing configured to receive a specimen pre-mounted in resin.

14. The system of claim 1, wherein the mounting station further comprises a plurality of specimen mounting cups, each cup having at least one indexing feature configured to angularly orient the cup within the mounting station.

15. The system of claim 14, wherein the at least one indexing feature on each cup indicates the angular orientation of the respective cup within the system.

16. The system of claim 15, wherein the automated transport assembly engages the at least one indexing feature on a specimen mounting cup to transport the cup in a predetermined orientation.

* * * * *